United States Patent [19]

Sasaki et al.

[11] Patent Number: 5,238,807
[45] Date of Patent: Aug. 24, 1993

[54] SILVER HALIDE PHOTOGRAPHIC MATERIAL

[75] Inventors: Hirotomo Sasaki; Tetsuro Kojima; Hiroyuki Mifune; Mikio Ihama, all of Kanagawa, Japan

[73] Assignee: Fuji Photo Film Co., Ltd., Kanagawa, Japan

[21] Appl. No.: 702,576

[22] Filed: May 20, 1991

[30] Foreign Application Priority Data

May 21, 1990 [JP] Japan .................................. 2-130976

[51] Int. Cl.$^5$ .............................................. G03C 1/09
[52] U.S. Cl. .................................... 430/600; 430/603; 430/567; 430/569
[58] Field of Search ................ 430/600, 603, 567, 569

[56] References Cited

U.S. PATENT DOCUMENTS

| | | | |
|---|---|---|---|
| 3,597,444 | 8/1971 | Klayman et al. | 548/300 |
| 4,749,646 | 6/1988 | Herz et al. | 430/603 |
| 4,810,626 | 3/1989 | Burgmaier et al. | 430/603 |
| 5,004,679 | 4/1991 | Orifumi et al. | 430/603 |
| 5,015,567 | 5/1991 | Suga et al. | 430/603 |
| 5,068,173 | 11/1991 | Takehara et al. | 430/567 |
| 5,087,555 | 2/1992 | Saiton | 430/567 |

FOREIGN PATENT DOCUMENTS 0280031 8/1988 European Pat. Off.
0282896 9/1988 European Pat. Off.

OTHER PUBLICATIONS

European Search Report 91 10 8205, Berlin, Jul. 19, 1991, H. Stock.
Chemical Abstracts, The American Chemical Society, vol. 98, 1983, p. 573, abstract #71469u, "The Chemical of thio-and selenocarbonic acids. 7. Preparation of tetrasubstituted selenoureas and pentasubstituted selenosemicarbazides from carbon diselenide".
Chemical Abstracts, The American Chemical Society, vol. 89, 1978, p. 898, abstract #109242u, "Synthesis of some N-substituted and N,N'-disubstituted 1,3-imidazolidine-2-selenones".

Primary Examiner—Charles L. Bowers, Jr.
Assistant Examiner—Thorl Chea
Attorney, Agent, or Firm—Sughrue, Mion, Zinn, Macpeak & Seas

[57] ABSTRACT

A silver halide photographic material low in fogging generation and high in sensitivity comprising a silver halide emulsion selenium sensitized with at least one compound selected from the group consisting of compounds represented by general formulae (I) and (III):

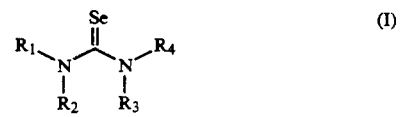

(I)

wherein each of $R_1$, $R_2$, $R_3$ and $R_4$ represents an alkyl group, a cycloalkyl group, an alkenyl group, an alkynyl group, an aralkyl group, an aryl group, a heterocyclic group, an acyl group, a carboxyl group, an alkoxycarbonyl group, an aryloxycarbonyl group, a carbamoyl group or a sulfamoyl group, provided that a tetramethylselenourea is excluded;

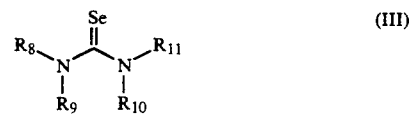

(III)

wherein each of $R_8$, $R_9$, $R_{10}$ and $R_{11}$ represents a hydrogen atom, an alkyl group, a cycloalkyl group, an alkenyl group, an alkynyl group, an aralkyl group, an aryl group, a heterocyclic group, an acyl group, a carboxyl group, a formyl group, an alkoxycarbonyl group, an aryloxycarbonyl group, a carbamoyl group or a sulfamoyl group, provided that at least one pair of $R_8$ and $R_9$, $R_9$ and $R_{10}$, $R_{10}$ and $R_{11}$, and $R_{11}$ and $R_8$ combine to form a ring.

10 Claims, No Drawings

SILVER HALIDE PHOTOGRAPHIC MATERIAL

FIELD OF THE INVENTION

The present invention relates to a silver halide photographic material, and more particularly to a silver halide photographic material containing a silver halide emulsion having improved fogging and sensitivity properties.

BACKGROUND OF THE INVENTION

Silver halide emulsions used in silver halide photographic materials are generally subjected to chemical sensitization by various chemical substances to obtain desired sensitivity and gradation levels. Sulfur sensitization, selenium sensitization, noble metal sensitization (for example, gold sensitization), reduction sensitization and combinations thereof are typical sensitization processes.

In recent years, high sensitivity, excellent graininess, high sharpness and rapid processing having an increased rate of development have been needed for the silver halide photographic materials. Accordingly, the above-described sensitizing processes have been improved.

Sensitization is disclosed in U.S. Pat. Nos. 1,574,944, 1,602,592, 1,623,499, 3,297,446, 3,297,447, 3,320,069, 3,408,196, 3,408,197, 3,442,653, 3,420,670 and 3,591,385, French Patents 2,093,038 and 2,093,209, JP-B-52-34491 (the term "JP-B" as used therein means an "examined Japanese patent publication"), JP-B-52-34492, JP-B-53-295, JP-B-57-22090, JP-A-59-180536 (the term "JP-A" as used herein means an "unexamined published Japanese patent application"), JP-A-59-185330,JP-A-59-181337,JP-A-59-187338,JP-A-59-192241, JP-A-60-150046, JP-A-60-151637, JP-A-61-246738, British Patents 255846 and 861984, and H. E. Spencer et al., *Journal of Photographic Science* 31, 158–169 (1983).

Although the selenium sensitization is generally higher in sensitizing effect than the sulfur sensitization more commonly employed in the art, it produces more fogging and tends to lower the contrast. Many of the above-described known patents attempt to overcome such disadvantages, but only insufficient results have been achieved. In particular, a basic improvement to depress the generation of fogging has been eagerly desired.

Further, when sulfur sensitization or the selenium sensitization is used in combination with gold sensitization, the sensitivity is significantly increased. However, fogging also increases at the same time. Compared to gold-sulfur sensitization, gold-selenium sensitization particularly increases fogging. For this reason, the development of techniques to depress the generation of fogging, particularly the development of selenium sensitizers generating less fogging, has been strongly desired.

SUMMARY OF THE INVENTION

One object of the present invention is to provide a silver halide photographic material which is low in fogging and high in sensitivity.

The above-described object of the present invention is achieved by a silver halide photographic material comprising a silver halide emulsion which has been selenium sensitized with at least one compound selected from the group consisting of compounds represented by the following general formulae (I) and (III):

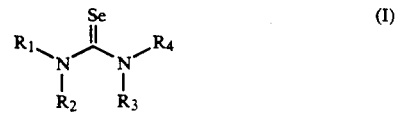

wherein each of $R_1$, $R_2$, $R_3$ and $R_4$ represents an alkyl group, a cycloalkyl group, an alkenyl group, an alkynyl group, an aralkyl group, an aryl group, a heterocyclic group, an acyl group, a carboxyl group, an alkoxycarbonyl group, an aryloxycarbonyl group, a carbamoyl group or a sulfamoyl group, provided that is a tetramethylselenourea is excluded. These groups may be the some of different. With thus material, it becomes possible to make full use of the sensitizing action of selenium sensitization which was difficult to realize by the prior art.

wherein each of $R_8$, $R_9$, $R_{10}$ and $R_{11}$ represents a hydrogen atom, an alkyl group, a cycloalkyl group, an alkenyl group, an alkynyl group, an aralkyl group, an aryl group, a heterocyclic group, an acyl group, a carboxyl group, a formyl group, an alkoxycarbonyl group, an aryloxycarbonyl group, a carbamoyl group or a sulfamoyl group, provided that at least one pair of $R_8$ and $R_9$, $R_9$ and $R_{10}$, $R_{10}$ and $R_{11}$, and $R_{11}$ and $R_8$ combine together to form a ring. These groups be the some of different.

DETAILED DESCRIPTION OF THE INVENTION

In general formula (I), each of $R_1$, $R_2$, $R_3$ and $R_4$ represents a substituted or unsubstituted alkyl group (for example, methyl, ethyl, n-propyl, t-butyl, isopropyl or n-octyl), a substituted or unsubstituted cycloalkyl group (for example, cyclopentyl, cyclohexyl or 2-methylcyclohexyl), a substituted or unsubstituted alkenyl group (for example, allyl, 2-butenyl or 3-pentenyl), a substituted or unsubstituted alkynyl group (for example, propargyl or 3-pentynyl), a substituted or unsubstituted aralkyl group (for example, benzyl or phenethyl), a substituted or unsubstituted aryl group (for example, phenyl, naphthyl or 4-methylphenyl), a substituted or unsubstituted heterocyclic group (for example, pyridyl, thienyl, furyl, imidazolyl, piperidyl or morpholyl), a substituted or unsubstituted acyl group (for example, acetyl, benzoyl, formyl or pivaloyl), a carboxyl group, a substituted or unsubstituted alkoxycarbonyl group (for example, methoxycarbonyl or ethoxycarbonyl), a substituted or unsubstituted aryloxycarbonyl group (for example, phenoxycarbonyl), a substituted or unsubstituted carbamoyl group (for example, carbamoyl, dimethylcarbamoyl or propylcarbamoyl), or a substituted or unsubstituted sulfamoyl group (for example, sulfamoyl or N-methylsulfamoyl).

The substituent groups on the $R_1$, $R_2$, $R_3$ and $R_4$ groups include: alkyl groups (for example, methyl ethyl and t-butyl), cycloalkyl groups (for example, cyclopentyl and cyclohexyl), heterocyclic groups (for example, pyridyl, thienyl, furyl, imidazolyl, piperidyl, morpholyl, benztriazolyl, benzoxazolyl, thiazolyl, tetrazolyl, tetraazaindenyl and indolyl), acyl groups (for example, acetyl, benzoyl, formyl and pivaloyl), a carboxyl group, alkoxycarbonyl groups (for example, methoxycarbonyl and ethoxycarbonyl), aryloxycarbonyl groups (for example, phenoxycarbonyl), acyloxy groups (for example, acetoxy and benzoyloxy), amino groups (for example, unsubstituted amino, dimethylamino and ethylamino), ammonio groups (for example, trimethylammonio), acylamino groups (for example, acetyl amino and benzoylamino), carbamoyl groups (for example, carbamoyl, dimethylcarbamoyl and propylcarbamoyl), sulfonylamino groups (benzenesulfonamido), sulfamoyl groups (for example, sulfamoyl and N-methylsulfamoyl), alkoxy groups (for example, methoxy, ethoxy and isopropoxy), aryloxy groups (for example, phenoxy), alkylthio groups (for example, methylthio and ethylthio), arylthio groups (for example, phenylthio), sulfonyl groups (for example, mesyl, and benzenesulfonyl), sulfinyl groups (for example, methylsulfinyl and ethylsulfinyl), a sulfo group, a sulfino group, a hydroxyl group, halogen groups (for example, fluoro, chloro and bromo atoms), a cyano group, a nitro group, ureido groups (for example, ureido and N'-methylureido), a phosphono group and a mercapto group, which may themselves be substituted.

Of the compounds represented by general formula (I), the compounds represented by the following general formula (II) are preferred:

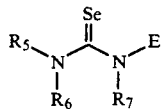

(II)

wherein each of $R_5$, $R_6$, $R_7$ and E represents an alkyl group, a cycloalkyl group, an alkenyl group, an alkynyl group, an aralkyl group, an aryl group, a heterocyclic group, an acyl group, a carboxyl group, an alkoxycarbonyl group, an aryloxycarbonyl group, a carbamoyl group or a sulfamoyl group, provided that E has a $\sigma p$ value of Hammett's constituent constant of $-0.1$ or more. These groups may be the some of different.

In general formula (II), $R_5$, $R_6$ and $R_7$ have the same meaning as $R_1$, $R_2$, $R_3$ and $R_4$ in general formula (I) having 1 to 30, preferably 1 to 20, most preferably 1 to 10 carbon atoms.

E represents a group having 1 to 30, preferably 1 to 20, most preferably 1 to 10 carbon atoms, such as a substituted or unsubstituted alkyl group (for example, chloromethyl, trifluoromethyl or acetonitrile), a substituted or unsubstituted cycloalkyl group (for example, cyclopentyl), a substituted or unsubstituted alkenyl group (for example, 1-chloro-3-butenyl or 1-chloro-4-octenyl), a substituted or unsubstituted alkynyl group (for example, 1-chloro-3-butynyl or 1-chloro-4-octynyl), a substituted or unsubstituted aralkyl group (for example, benzyl), a substituted or unsubstituted aryl group (for example, phenyl or pentafluorophenyl), a substituted or unsubstituted heterocyclic group (for example, 4-pyridyl, 2-benzoxazolyl or 1-ethyl-2-benzimidazolyl), a substituted or unsubstituted acyl group (for example, acetyl, formyl, benzoyl or pivaloyl), a carboxyl group, a substituted or unsubstituted alkoxycarbonyl group (for example, methoxycarbonyl or ethoxycarbonyl), a substituted or unsubstituted aryloxycarbonyl group (for example, phenoxycarbonyl), a substituted or unsubstituted carbamoyl group (for example, carbamoyl, dimethylcarbamoyl or propylcarbamoyl), or a substituted or unsubstituted sulfamoyl group (for example, sulfamoyl or methylsulfamoyl). These groups have a $\sigma p$ value of Hammett's constituent constant [Journal of Medicinal Chemistry 16, 304 (1973) and ibid. 20, 304 (1977)] of $-0.1$ or more.

The substituent groups on the $R_5$, $R_6$, $R_7$ and E groups are those mentioned as substituents for the $R_1$, $R_2$, $R_3$ and $R_4$ groups in general formula (I).

In general formula (I), each of $R_1$, $R_2$ and $R_3$ preferably represents a substituted or unsubstituted alkyl group, a substituted or unsubstituted aryl group, a substituted or unsubstituted heterocyclic group or a substituted or unsubstituted acyl group. $R_4$ is preferably a substituted or unsubstituted heterocyclic group, a substituted or unsubstituted acyl group, a substituted or unsubstituted carbamoyl group, a substituted alkyl group or a substituted aryl group, which has a $\sigma p$ value of Hammett's substituent constant of 0.3 or more.

More preferably, each of $R_1$, $R_2$ and $R_3$ represents a substituted or unsubstituted alkyl group, a substituted or unsubstituted aryl group, or a substituted or unsubstituted acyl group. $R_4$ is more preferably an acyl group having a $\sigma p$ value of Hammett's substituent constant of 0.5 or more.

In general formula (III), each of $R_8$, $R_9$, $R_{10}$ and $R_{11}$ represents a hydrogen atom, or a groups having 1 to 30, preferably 1 to 20, most preferably 1 to 10 carbon atoms, such as, a substituted or unsubstituted alkyl group (for example, methyl, ethyl, n- propyl, t-butyl, isopropyl or n-octyl), a substituted or unsubstituted cycloalkyl group (for example, cyclopentyl, cyclohexyl or 2-methylcyclohexyl), a substituted or unsubstituted alkenyl group (for example, allyl, 2-butenyl or 3-pentenyl), a substituted or unsubstituted alkynyl group (for example, propargyl or 3-pentynyl), a substituted or unsubstituted aralkyl group (for example, benzyl or phenethyl), a substituted or unsubstituted aryl group (for example, phenyl, naphthyl or 4-methylphenyl), a substituted or unsubstituted heterocyclic group (for example, pyridyl, thienyl, furyl, imidazolyl, piperidyl or morpholyl), a substituted or unsubstituted acyl group (for example, acetyl, benzoyl, formyl or pivaloyl), a carboxyl group, a substituted or unsubstituted alkoxycarbonyl group (for example, methoxycarbonyl or ethoxycarbonyl), a substituted or unsubstituted aryloxycarbonyl group (for example, phenoxycarbonyl), a substituted or unsubstituted carbamoyl group (for example, carbamoyl, dimethylcarbamoyl or propylcarbamoyl), or a substituted or unsubstituted sulfamoyl group (for example, sulfamoyl or methylsulfamoyl).

Groups which combine with other groups to form rings include substituted or unsubstituted alkylene groups (for example, methylene, ethylene, propylene, butylene, hexylene, 1-methylethylene, —CH₂CH₂OCH₂CH₂— and —CH₂CH₂NHCH₂CH₂— groups, which may contain ether, thioether, substituted or unsubstituted amino groups), substituted or unsubstituted aralkylene groups (for example, benzylidene), substituted or unsubstituted arylene groups (for example, phenylene and naphthylene), substituted or unsubstituted heterocyclic linking groups (for example, 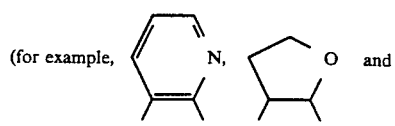

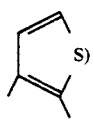

and linking groups, linked thereto (for example, 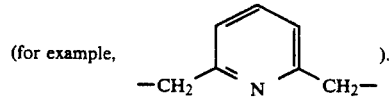 ).

The substituent groups on the $R_8$, $R_9$, $R_{10}$ and $R_{11}$ groups include the substituent groups on the $R_1$, $R_2$, $R_3$ and $R_4$ groups in general formula (I).

In general formula (III), rings formed by $R_8$ and $R_9$, $R_9$ and $R_{10}$, $R_{10}$ and $R_{11}$, and $R_{11}$ and $R_8$ are preferably 4- to 7-membered rings. $R_8$, $R_9$, $R_{10}$ and $R_{11}$ are preferably hydrogen atoms, substituted or unsubstituted alkyl groups, substituted or unsubstituted aryl groups, substituted or unsubstituted heterocyclic groups, substituted or unsubstituted acyl groups and substituted or unsubstituted carbamoyl groups.

In general formula (III), more preferably, the rings formed by $R_8$ and $R_9$, $R_9$ and $R_{10}$, $R_{10}$ and $R_{11}$, and $R_{11}$ and $R_8$ are 5- or 6-membered rings, and $R_8$, $R_9$, $R_{10}$ and $R_{11}$ are preferably hydrogen atoms, substituted or unsubstituted alkyl groups and substituted or unsubstituted aryl groups.

Examples of the compounds used in the present invention are shown below, but the compounds used in the present invention are not limited thereto:

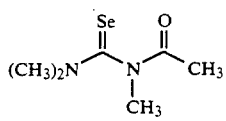 I-1

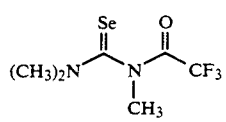 I-2

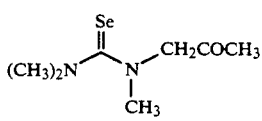 I-3

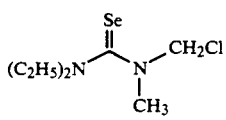 I-4

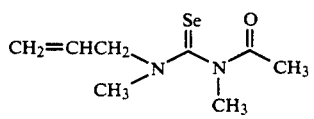 I-5

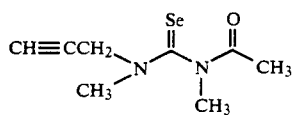 I-6

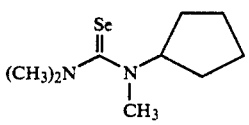 I-7

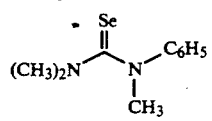 I-8

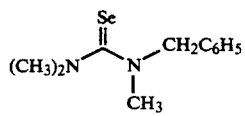 I-9

 I-10

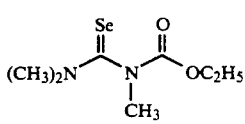 I-11

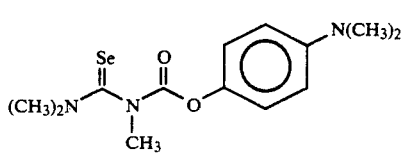 I-12

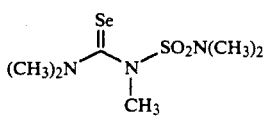 I-13

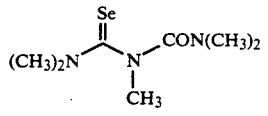 I-14

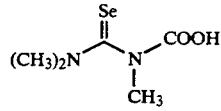 I-15

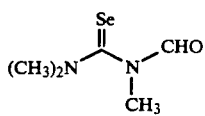 I-16

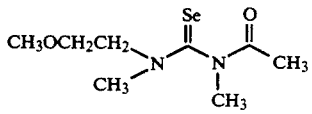 I-17

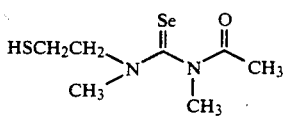 I-18

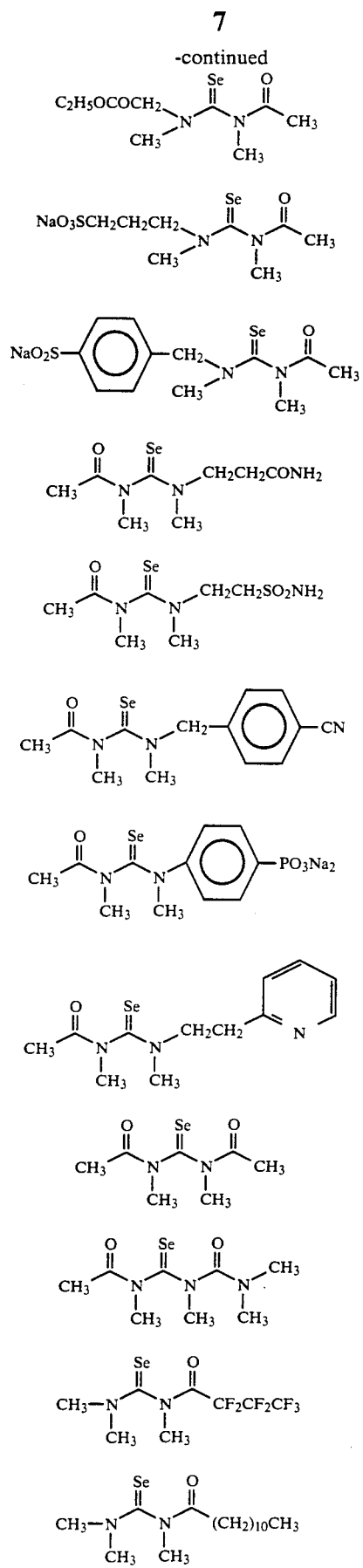
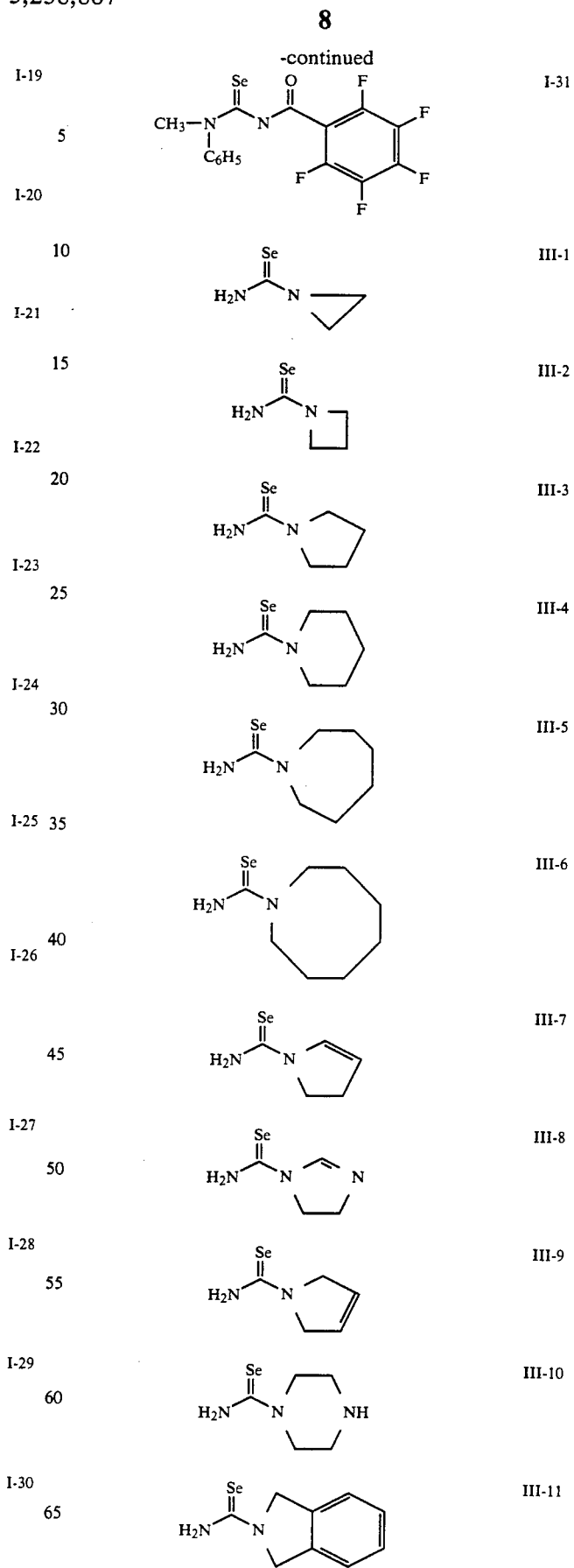

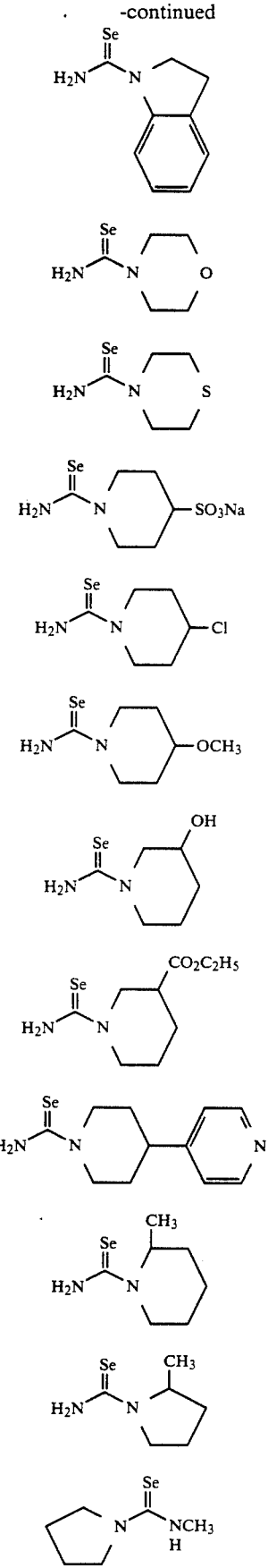
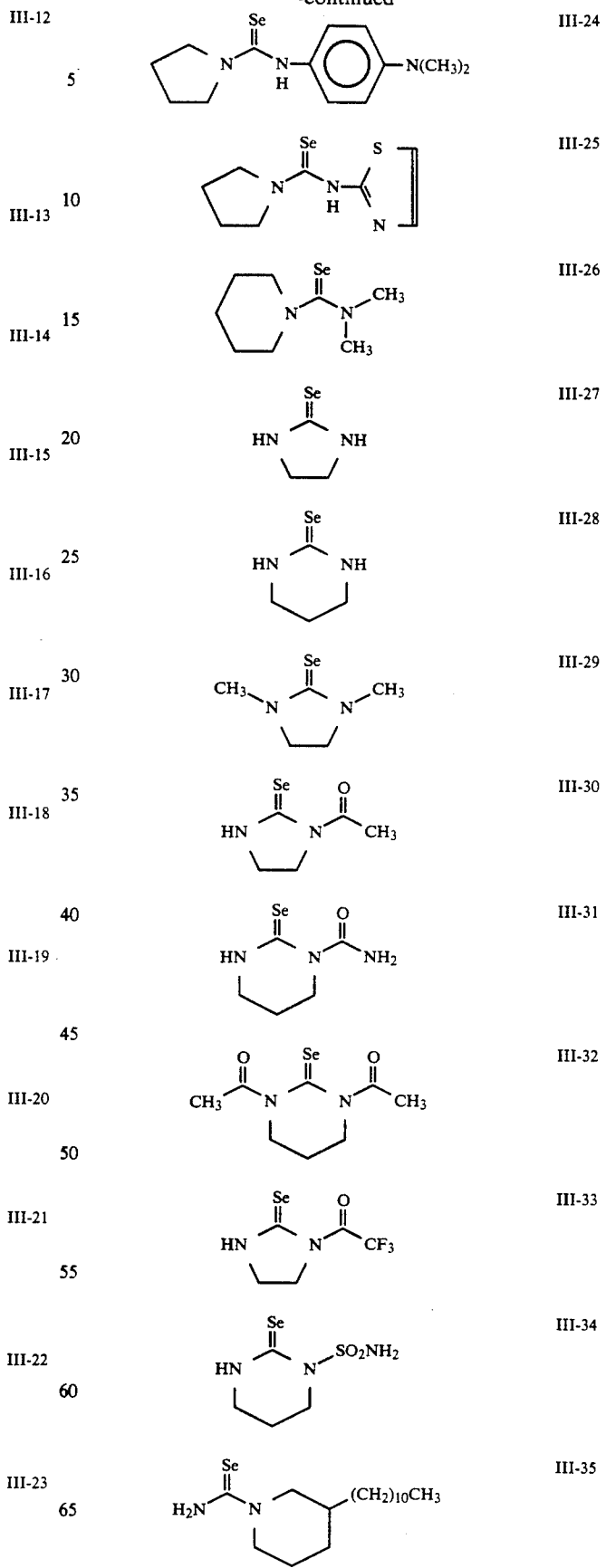

-continued

III-36 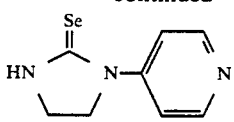

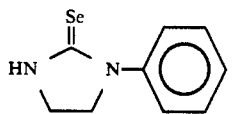

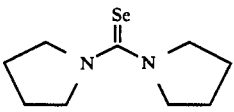

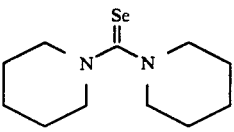

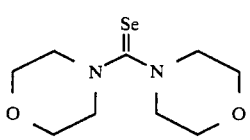

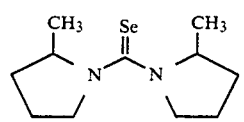

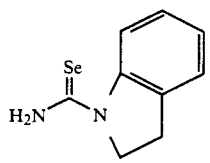

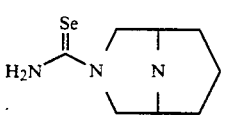

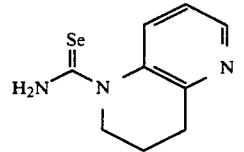

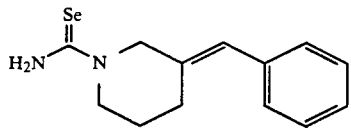

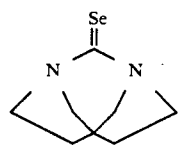

-continued

III-47 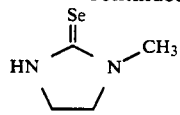

The compounds represented by general formulae (I) and (III) can be synthesized in accordance with known methods, namely the methods described in *The Chemistry of Organic Selenium and Tellurium Compounds*, edited by Saul Patai, vol. 2, pages 255-258 (1987).

These compounds may generally be synthesized by a method comprising s-alkylating a thiourea compound followed by reacting with a sodium hydrogenselenate, or reacting a cyanamide compound with hydrogenselenate.

With respect to the synthesis of the compounds represented by general formulae (I) and (III), typical synthesis examples are described below.

SYNTHESIS EXAMPLE 1

Synthesis of Compound I-1

1-(1) Synthesis of N-Acetyl-N,N', N'-Trimethylthiourea:

To 400 ml of a toluene solution containing 40 g of N,N,N'-trimethylthiourea, 37 g of acetic anhydride was added, and 0.5 ml of concentrated sulfuric acid was subsequently added thereto with stirring. The resulting reaction solution was heated to a temperature of 80° C. and stirred for 6 hours, followed by cooling to room temperature. A products was extracted to water layer by adding 400 ml of water. To the water layer separated, NaCl was added to form a saturated NaCl solution. Thereafter, extraction was conducted by acetonitrile, and the resulting acetonitrile layer was dried with magnesium sulfate, followed by concentration to obtain the desired product. The product was oily and the yield was 42 g.

1-(2) Synthesis of N-Acetyl-N,N',N', S-Tetramethylthiouronium Iodide;

Forty-two g of N-acetyl-N,N',N'-trimethylthiourea obtained in 1-(1) was dissolved in 90 g of iodomethane, and stirred at room temperature for 8 hours. The resulting crystals were collected by filtration and washed with chloroform to obtain the desired product. The yield was 23 g.

1-(3) Synthesis of Compound I-1:

Under a nitrogen gas atmosphere, 2.0 g of selenium was added to 150 ml of dry ethanol. After cooling this product to 0° C., 1.0 g of sodium boron hydride was added thereto with stirring. Immediately, a gas began to generate and subsided after several minutes. Stirring was further continued at room temperature for several minutes. As a result, a light-red NaHSe solution was obtained. Then, 50 ml of an ethanol solution containing 4.0 g of N-acetyl-N,N',N', S-tetramethylthiouronium iodide was added to this solution, followed by standing at room temperature for 20 hours. The resulting solution was made weakly acidic by adding glacial acetic acid, and then concentrated to 70 ml under reduced pressure.

The concentrated solution was extracted with chloroform and water, and the chloroform layer was concentrated to dryness. The resulting crystals were recrystalized from a 15 ml-10 ml ethyl acetate-hexane mixed solvent to obtain 2.3 g of the desired example compound I-1.

The nuclear magnetic resonance spectrum, the mass spectrum and elemental analysis of the desired product agreed with expected results. The yield was 80% and the melting point was 87° to 88° C.

SYNTHESIS EXAMPLE 2

Synthesis of Compound III-29

2-(1) Synthesis of N,N'-Dimethylethylenethiouronium Iodide:

Thirty g of iodomethane was added to an acetone solution containing 20 g of N,N'-dimethylethylenethiourea, and stirred at room temperature for 8 hours. The formed crystals were collected by filtration, and washed with acetone to obtain the desired product. The yield was 32 g.

2-(2) Synthesis of Compound III-29

Two g of the desired example compound III-29 was obtained from 4.0 g of N,N'-dimethylethylenethiouronium iodide obtained in 2-(1) in a manner similar to that of Synthesis Example 1. The nuclear magnetic resonance spectrum, the mass spectrum and elemental analysis of the desired product agreed with expected results. The yield was 76% and the melting point was 144° to 145° C.

Other exemplory compounds can also be synthesized in a manner similar to these examples.

No specific example the the compound represented by general formula (I) or (III) being used as a selenium sensitizer has been reported until now. It has therefore been very difficult to anticipate the sensitizing action, the fogging and other photographic actions caused by these compounds. However, significant effects are obtained by using these compounds.

The amount of these selenium sensitizers used in this invention varies depending on the kind of selenium compounds and silver halide particles to be used and the conditions of chemical ripening, but is generally about $10^{-8}$ to $10^{-4}$ mol/mol of silver halide and preferably about $10^{-7}$ to $10^{-5}$ mol/mol of silver halide.

The conditions for chemical ripening are not particularly limited in the present invention. However, the pAg is 6 to 11, preferably 7 to 10, and more preferably 7 to 9.5. The temperature is 40° to 95° C., and preferably 50° to 85° C.

In the present invention, it is preferred to use the selenium sanitizers in combination with noble metal sensitizers such as gold, platinum, palladium and iridium sensitizers. In particular, the gold sensitizers are preferred. Specific examples thereof include chloroauric acid, potassium chloroaurate, potassium aurothiocyanate, gold sulfide and gold selenide. The gold sensitizers can be used in an amount of about $10^{-7}$ to $10^{-2}$ mol/mol of silver halide.

Further, it is also preferred to use the selenium sensitizers in combination with sulfur sensitizers in this invention. Specific examples thereof include conventional unstable sulfur compounds such as thiosulfates (for example, hypo), thioureas (for example, diphenylthiourea, triethylthiourea and allylthiourea) and rhodanine compounds. The sulfur sensitizers can be used in an amount of about $10^{-7}$ to $10^{-2}$ mol/mol of silver halide.

Furthermore, in the present invention, reduction sensitizers can also be used. Specific examples thereof include stannous chloride, aminoiminomethanesulfinic acid, hydrazine derivatives, borane compounds, silane compounds and polyamine compounds.

Moreover, in the present invention, it is preferred to conduct selenium sensitization in the presence of solvents for silver halides.

Specific examples of such solvents include thiocyanates (for example, potassium thiocyanate), thioether compounds (for example, the compounds described in U.S. Pat. Nos. 3,021,215 and 3,271,157, JP-B-58-30571 and JP-A-60-136736, particularly 3,6-dithia-1,8-octanediol),tetrasubstituted thiourea compounds (for example, the compounds described in JP-B-59-11892 and U.S. Pat. No. 4,221,863, particularly tetramethylthiourea), the thione compounds described in JP-B-60-11341, the mercapto compounds described in JP-B-63-29727, the mesoionic compounds described in JP-A-60-163042, the selenoether compounds described in U.S. Pat. No. 4,782,013, the telluroether compounds described in JP-A-2-118566 and sulfites. Of these compounds, particularly, thiocyanates, thioether compounds, tetra-substituted thiourea compounds and thione compounds can be preferably used. These compounds can be used in an amount of about $10^{-5}$ to $5\times10^{-2}$ mol/mol of silver halide.

The silver halide emulsion of the present invention preferably comprises silver bromide, silver iodobromide, silver iodochlorobromide, silver chlorobromide or silver chloride.

The silver halide grains of the present invention may have a regular crystal form such as a cubic, octahedral or tetradecahedral form, irregular crystal form (such as a spherical or a tabular form), or a composite form thereof. Further, mixtures of grains having various crystal forms may also be used. It is, however, preferred that the grains having a regular crystal form are used.

The silver halide grains used in the present invention may have different phases in the interior and the surface layers, respectively, or may have homogeneous phases. Further, the grains on the surfaces on which latent images are mainly formed (for example, negative type emulsions) may be used, or the grains in the interiors of which latent images are mainly formed (for example, internal latent image type emulsions or previously fogged direct reversal type emulsions) may be used. Preferably, the grains on the surfaces of which latent images are mainly formed are used.

The silver halide emulsions used in the present invention are preferably tabular grain emulsions which contain grains having a thickness of 0.5 microns or less, preferably 0.3 microns or less, and a diameter of preferably 0.6 microns or more, and in which 50% or more of all grains as a projected area are composed of grains having a mean aspect ratio of at least 5, or monodisperse emulsions having a statistical coefficient of variation (the value $S/\bar{d}$ obtained by dividing the standard deviation S by the diameter $\bar{d}$ in distribution of grains when the grain diameter is represented by the diameter of circles approximated by the projected area of the grains) of 20% or less. In addition, at least two kinds of tabular grain emulsions and monodisperse emulsions may be mixed.

The emulsions used in the present invention contain tabular silver halide grains having an aspect ratio of at least 3, and preferably a mean aspect ratio of 3 to almost 8. The term "tabular grain" is a general type of grain having one twin plane or at least two parallel twin planes. In this case, the twin plane means a (111) plane on both sides of which all lattice point ions are arranged in the mirror image relationship. This tabular grain shows a triangular, hexagonal or rounded circular form when observed from above. The triangular, hexagonal and circular grains have triangular, hexagonal and circular outer surfaces parallel to each other, respectively.

The aspect ratio of the tabular grains in the present invention means the value obtained by dividing the grain diameter by the thickness thereof, for each of the tabular grains having a grain diameter of 0.1 μm or more. The thickness of the grain can be easily measured by depositing a metal on the grain as well as a latex for reference from an oblique direction, measuring the length of its shadow under an electron microscope, and calculating by reference to the length of the shadow of the latex.

The grain diameter in the present invention is a diameter of a circle having an area equal to the projected area of the parallel outer surface of the grain.

The projected area of the grain can be obtained by measuring an area of the grain under an electron microscope, and then correcting the photographed magnification.

The diameter of the tabular grains is preferably 0.15 to 5 μm, and the thickness thereof is preferably 0.05 to 1.0 μm.

The mean aspect ratio is determined as an arithmetic mean of aspect ratios of at least 100 silver halide grains. Further, it can also be determined as a ratio of the mean diameter to the mean thickness of the grains.

The emulsions used in the present invention contain the tabular grains having an aspect ratio of at least 3, and preferably having a mean aspect ratio of 3 to almost 8.

It is preferred that the tabular grains account for 50% or more of all the projected areas, and particularly 80% or more.

In some cases, the use of tabular monodisperse grains gives more favorable effects. The structure and production of the tabular monodisperse grains are described in, for example, JP-A-63-151618. Briefly referring to the form thereof, 70% or more of all the projected areas of the silver halide grains are occupied by tabular silver halide grains in a hexagonal form having a ratio of the length of the longest side to that of the shortest side of 2 or less, and having two parallel surfaces as outer surfaces. Further, the coefficient of variation of grain size distribution of the hexagonal tabular silver halide grains [the value obtained by dividing the variation of the grain size represented by the diameter of the projected areas converted to circles (standard deviation) by the mean grain size] is 20% or less and has a monodisperse property.

Furthermore, the emulsion grains used in the present invention have transitions.

The transition of tabular grains can be observed by the direct method using a transmission electron microscope at low temperatures, described in, for example, J. F. Hamilton, *Phot. Sci. Eng.* 11, 57 (1967) and T. Shiozawa, *J. Soc. Phot. Sci. Japan* 35, 213 (1972). Namely, the silver halide grains taken out of the emulsion with caution so as not to apply too much pressure so that the transition is produced in the grains, are placed on a mesh for an electron microscope. The sample grains are observed by the transmission method under cooling to prevent damage due to the electron beams (for example, a printout). In that case, electron beam transmission becomes difficult as the thickness of the grains increases. Accordingly, the use of a high-voltage type electron microscope (200 kv or more to a 0.25 μm-thick grain) makes it possible to observe the grains more clearly. From the grain photograph obtained by this method, the position and the number of the transitions observed from a vertical direction to a main plane can be determined.

The number of transition lines is at least one/grain, preferably at least 10/grain, and more preferably at least 20/grain, on average. When the transition lines are dense, or when the transition lines cross one another, the number of transition lines per grain can not always be counted definitely. Also in these cases, however, the lines can be roughly counted, such as 10 lines, 20 lines and 30 lines, so that they are distinguishable from the case that only several lines exist. The mean number of transition lines per grain is determined by counting the number of transition lines for at least 100 grains and calculating a number average value.

For example, a transition line can be introduced into the vicinity of the outer periphery of the tabular grain. In this case, the transition line is approximately vertical to the outer periphery, and generated so that it starts from a position x% of the distance from the center of the tabular grain to the outer periphery and reaches the outer periphery. This value of x is preferably 10 to less than 100, more preferably 30 to less than 99, and most preferably 50 to less than 98. The configuration formed by connecting positions at which the transition is initiated is similar to a figure of the grain form, but is sometimes distorted and does not form a completely similar figure. The transition of this type can not be observed in a center region of the grain. The direction of the transition lines is approximately a (211) direction, crystallographically. However, the transition lines often snake or cross one another.

The tabular grain may have transition lines uniformly throughout the whole region of the outer periphery, or may have them locally on the outer periphery. Namely, taking the case of the hexagonal tabular silver halide grain, the transition lines may be restricted to only the vicinity of the 6 vertices, or only to the vicinity of one vertex. On the contrary, the transition lines can also be restricted to only the sides, any from the vicinity of the 6 vertices.

Further, the transition lines may be formed along a region containing centers of two parallel main planes of the tabular grain. When the transition lines are formed throughout the whole region of the main plane, the direction of the transition lines is sometimes formed in an approximately (211) direction, crystallographically, observed from a vertical direction to the main plane. However, the transition lines are formed in a (110) direction or randomly in some cases. In this latter case, the length of each transition line is random. Accordingly, some lines are observed as short lines on the main plane and some lines are observed as long lines reaching the sides (i.e., the outer periphery). The transition lines are linear or often snake. In many cases, they cross one another.

Although the position of the transitions may be restricted on the outer periphery, the main plane or the local positions as described above, the transition lines may be located in combinations thereof. Namely, the transition lines may exist on the outer periphery and the main plane at the same time.

The introduction of the transition lines onto the outer periphery of the tabular gain can be achieved by forming a specific highly concentrated silver iodide layer in the grain. The highly concentrated silver iodide layer defined here contains highly concentrated silver iodide regions discontinuously formed. Specifically, a base grain is prepared, and then the high silver iodide content layer is provided thereon. The outside thereof is covered with a layer lower in silver iodide content than the highly concentrated silver iodide layer. The silver iodide content of the tabular base grain is lower than that of the highly concentrated silver iodide layer. The silver iodide content is preferably 0 to 20 mol %, and more preferably 0 to 15 mol %.

The expression "highly concentrated silver iodide layer in a grain" means a silver halide solid solution containing silver iodide. In this case, preferred examples of the silver halides include silver iodide, silver iodobromide and silver chloroiodobromide. Silver iodide or silver iodobromide (wherein the content of silver iodide is 10 to 40%) is more preferable. To locate this highly concentrated silver iodide layer in the grain (hereinafter referred to as the internal highly concentrated silver iodide layer) on either the side or the corner of the base grain selectively, the forming conditions of the base grain and the internal highly concentrated silver iodide layer must be controlled. The forming conditions of the base grain include: pAg (the logarithm of the reciprocal of the silver ion concentration); the presence or absence, kind and amount of a solvents for the silver halide; and the temperature. The internal highly concentrated silver iodide layer can be located selectively in the vicinity of the vertex of the base grain by adjusting the pAg to 8.5 or less, more preferably 8 or less, at the time of growth of the base grain. On the other hand, the internal highly concentrated silver iodide layer can be located on the side of the base grain by adjusting the pAg to 8.5 or more, more preferably 9 or more, at the time of growth of the base grain. The threshold value of the pAg varies up and down depending on the temperature and the presence or absence, kind and amount of the solvent for the silver halide. For example, when a thiocyanate was used as the solvent for the silver halide, the threshold value of the pAg is shifted to a higher value. Among the various pAg values over the time of the growth, the pAg at the last stage of growth of the grain is most important. On the other hand, even when the pAg at the time of the growth does not satisfy the above-described value, the location the internal high concentrated silver iodide layer can be controlled by adjusting the pAg to the above-described value after the growth of the base grain, followed by ripening. At this time, ammonia, an amine compound or a thiocyanate is effective as the solvent for the silver halide. For the formation of the internal highly concentrated silver iodide layer, the so-called conversion methods can be employed. These methods include the method of adding halogen ions during grain formation which form silver salts lower in solubility at that time than the grains or halogen ions forming the vicinity of the surfaces of the grains. In the present invention, it is preferred that the halogen ions lower in solubility are added in an amount of a certain value related to the halogen composition or related to the surface area of the grains at that time. For example, in the course of grain formation, it is preferred that KI is added in an amount of a certain figure or more based on the surface area of AgBr grains at that time. Specifically, it is preferred that an iodide salt is added in an amount of $8.2 \times 10^{-5}$ mol/m$^2$ or more.

More preferably, the internal highly concentrated silver iodide layer is produced by adding an aqueous solution of a halide salt containing an iodide salt and simultaneously adding an aqueous solution of a silver salt.

For example, an aqueous solution of KI is added and simultaneously an aqueous solution of AgNO$_3$ is added by a double jet method. The addition time of either the aqueous solution of KI or the aqueous solution of AgNO$_3$ may come first. Similarly, the addition terminating time of either the KI or the AgNO$_3$ solutions may come first. The addition mol ratio of the aqueous solution of AgNO$_3$ to the aqueous solution of KI is preferably 0.1 or more, more preferably 0.5 or more, and most preferably 1 or more. The total added mol amount of the aqueous solution of AgNO$_3$ may be in the silver excess region to the halogen ions and the added iodine ions in the system. When the aqueous solution of the halide salt containing the iodide salt and the aqueous solution of the silver salt are added by the double jet method, it is preferred that the pAg decreases over the addition time by the double jet method. The pAg before the initiation of addition is preferably 6.5 to 13, and more preferably 7.0 to 11. When the addition is terminated, the pAg is most preferably 6.5 to 10.0.

When the above-described methods are carried out, it is preferred that the solubility of the silver halide in the mixture system is as low as possible. When the high concentrated silver iodide layer is formed, therefore, the temperature of the mixture system is preferably 30° to 70° C., and more preferably 30° to 50° C.

Most preferably, the internal highly concentrated silver iodide layer can be formed by adding fine-grain silver iodide (which means finely divided silver iodide, the same applies hereinafter), fine-grain silver iodobromide, fine-grain silver chloroiodide or fine-grain silver chloroiodobromide. In particular, the addition of fine-grain silver iodide is preferable. The size of these fine grains is usually 0.01 to 0.1 μm. However, the fine grains having a grain size of less than 0.01 μm or more than 0.1 μm can also be used. The methods of preparing these finely divided silver halide grains are described in JP-A-1-183417, JP-A-2-44335, JP-A-1-183644, JP-A-1-183645, JP-A-2-43534 and JP-A-2-43535. The internal highly concentrated silver iodide layer can be formed by addition of the fine silver halide grains and ripening. When the fine grains are dissolved by ripening, the above-described solvent for the silver halide can also be used. It is not necessary for these added fine grains all to be immediately dissolved to disappear. It is sufficient that they be dissolved when the end grains are completed.

The outer layer covering the internal highly concentrated silver iodide layer is lower in silver iodide content than the internal highly concentrated silver iodide layer. The silver iodide content of the outer layer is preferably 0 to 30 mol %, more preferably 0 to 20 mol %, and most preferably 0 to 10%. It is preferred that this internal highly concentrated silver iodide layer is positioned within a circular region containing 5 to almost 100 mol % of the silver amount of the whole grain when measured from the center of a hexagonal form or the like formed by projection of the grain. More preferably, this layer exists within a circular region containing 20 to almost 95 mol %, particularly 50 to almost 90 mol % of the silver content. The amount of the silver halide forming the internal highly concentrated silver iodide layer, as the amount of silver, is 50 mol % or less of the silver content of the whole grain, and more preferably 20 mol % or less. These values with respect to the internal highly concentrated silver iodide layer are formulation values for producing the silver halide emulsion, and values obtained by measuring the halogen composition at the end grain by various analyzing methods. In the end grain, the internal highly concentrated silver iodide layer often disappears during the recrystallization course or the like. The above description relates to the production thereof.

Accordingly, although the transition lines in the end grain can be easily observed by the above-described methods, the internal highly concentrated silver iodide layer introduced for introduction of transition lines can not be confirmed as a clear layer in many cases. For example, the outer peripheral regions of the tabular grain are all observed as the internal highly concentrated silver iodide layer in some cases. The halogen composition thereof can be confirmed by combinations of an X-ray diffraction method, an EPMA (also called XMA) method (a method in which silver halide composition is detected by scanning silver halide grains with electron beams) and an ESCA (also called XPS) method (a method in which grains are irradiated with X-rays and photo-electrons emitted from the surfaces of the grains are spectrally dispersed).

The outer layer covering the internal highly concentrated silver iodide layer may be formed at any temperature and at any pAg. However, the temperature is preferably 30° to 80° C., and most preferably 35° to 70° C. The pAg is preferably 6.5 to 11.5. In some cases, the conventional solvent well known in the arts for the silver halide is preferably used. A thiocyanate salt is most favorable as the solvent for the silver halide.

The transition lines are introduced onto the main plane of the tabular grain by preparing the base grain, depositing a silver halochloride on the main plane, forming an internal highly concentrated silver bromide layer or an internal highly concentrated silver iodide layer by conversion of the silver halochloride, and forming a shell on the outside thereof. The silver halochlorides include silver chloride, silver chlorobromide containing silver chloride in an amount of 10 mol % or more, preferably in an amount of 60 mol % or more, and silver chloroiodobromide. Each of these silver halochlorides can be deposited on the main plane of the base grain by adding an aqueous solution of silver nitrate and an aqueous solution of an appropriate alkaline metal salt separately or simultaneously, or by adding an emulsion containing these silver salts, followed by ripening. These silver halochlorides can be deposited over the whole pAg range. However, the range from 5.0 to 9.5 is most desirable. In this method, the tabular grain is allowed to grow in a thickness direction. The amount of this silver halochloride layer is 1 to 80 mol %, and more preferably 2 to 60 mol %, in mol % of silver, based on the base grain. This silver halochloride layer is converted with an aqueous solution of a halide which can form a silver salt lower in solubility than the silver halochloride, whereby the transition lines can be introduced onto the main plane of the tabular grain. For example, this silver halochloride layer is converted with the aqueous solution of KI, and then a shell is allowed to grow. Thus, the end grain can be obtained.

The halogen conversion of the silver halochloride layer does not mean that the silver halochloride is all replaced by a silver salt lower in solubility than the silver halochloride. The silver halochloride is replaced by a silver salt lower having solubility in an amount of preferably 5% or more, more preferably 10% or more, most preferably 20% or more. The transition lines can be introduced into local sites on the main plane by controlling the halogen structure of the base grain to be provided with the silver halochloride layer. For example, if a base grain is used which is displaced in a lateral direction of the tabular base grain and has the external highly concentrated silver iodide structure, the transition lines can be introduced only into the central portion, but not the peripheral portion of the main plane. Further, using a substance for locally controlling the epitaxial growth of a silver halochloride, for example, an iodide, it is also possible to deposit the silver halochloride only on a site restricted for the introduction of the transition line. It is preferred that the silver halochloride is deposited at a temperature of 30° to 70° C., and more preferably 30° to 50° C. It is also possible to carry out the conversion after deposition of the silver halochloride, followed by growth of the shell. However, it is also possible to conduct halogen conversion while allowing the shell to grow after deposition of the silver halochloride.

It is preferred that the internal highly concentrated silver iodide layer formed approximately parallel with the main plane is positioned within a circular region containing 5 to almost 100 mol % of the silver amount of the whole grain, from the center of the thickness of the grain. More preferably, this layer exists within a circular region containing 20 to almost 95 mol %, particularly 50 to almost 90 mol %, of the silver content.

This silver iodide content of the shell is preferably 0 to 30 mol %, and more preferably 0 to 20 mol %. The shell may be formed at any temperature and at any pAg. However, the temperature is preferably 30° to 80° C., and most preferably 35° to 70° C. The pAg is preferably 6.5 to 11.5. In some cases, the conventional solvent well known in the arts for the silver halide is preferably used. A thiocyanate salt is most favorable as the solvent for the silver halide.

In the end grain, the internal highly concentrated silver iodide layer subjected to the halogen conversion can not be confirmed by the above-described halogen composition analyzing methods, depending on various conditions such as the degree of halogen conversion in some cases. However, the transition lines can be clearly observed. The transition lines can also be introduced by the methods for introducing the transition lines onto any positions on the main plane of the tabular grain, in combination with the methods for introducing the transition lines onto any positions on the outer periphery of the above-described tabular grain.

Preferred examples of the silver halides include silver iodobromide containing 30 mol % or less of silver iodide, and silver iodochlorobromide.

The tabular grains used in the present invention can be easily prepared according to the methods described in Cleve, *Photography Theory and Practice*, page 131 (1930), Gutoff, *Photographic Science and Engineering* 14, 248-257 (1970), U.S. Pat. Nos. 4,434,226, 4,414,310, 4,433,048 and 4,439,520, and British Patent 2,112,157.

The photographic emulsions used in the present invention can be prepared according to the methods described in P. Glafkides, *Chimie et Physique Photographique* (Paul Montel, 1967), G. F. Duffin, *Photographic Emulsion Chemistry* (Focal Press, 1966), and V. L. Zelikman et al., *Making and Coating Photographic Emulsion* (Focal Press, 1964).

In forming the silver halide grain emulsions, the solvents for silver halides are used to control the growth of the grains. Examples of such solvents include ammonia, potassium rhodanide, ammonium rhodanide and thioether compounds (for example, described in U.S. Pat. Nos. 3,271,157, 3,574,628, 3,704,130, 4,297,439 and 4,276,374), thione compounds (for example, described in JP-A-53-144319, JP-A-53-82408 and JP-A-55-77737) and amine compounds (for example, described in JP-A-54-100717).

Cadmium salts, zinc salts, thallium salts, iridium salts or complex salts thereof, rhodium salts or complex salts thereof, iron salts or complex salts thereof may coexist during the formation of the silver halide grains or during physical ripening.

Gelatin can be advantageously used as a binder or a protective colloid which can be used in the emulsion layers or the intermediate layers of the photographic material of the present invention. However, hydrophilic colloids other than gelatin may also be used. For example, various synthetic hydrophilic polymers can be used. Examples of such polymers include proteins such as gelatin derivatives, graft polymers of gelatin and other polymers, albumin and casein; cellulose derivatives such as hydroxyethyl cellulose, carboxymethyl cellulose and cellulose sulfate; saccharide derivatives such as sodium alginate and starch derivatives; and homopolymers or copolymers such as polyvinyl alcohol, partially acetalized polyvinyl alcohol, poly-N-vinylpyrrolidone, polyacrylic acid, polymethacrylic acid, polyacrylamide, polyvinylimidazole and polyvinylpyrazole.

As gelatin, acid-treated gelatin or enzyme-treated gelatin described in Bull. Soc. Sci. Phot. Japan 16, 30 (1966), as well as general-purpose lime-treated gelatin, may also be used. Further, hydrolyzed products of gelatin can be used.

In the photographic materials of the present invention, inorganic or organic hardening agents may be added to any hydrophilic colloid layers constituting photographic light-sensitive layers or back layers. Specific examples thereof include chromium salts, aldehydes (such as formaldehyde, glyoxal and glutaraldehyde) and N- methylol compounds (such as dimethylolurea). Active halogen compounds (such as 2,4-dichloro-6-hydroxy-1,3,5-triazine and the sodium salt thereof) and active vinyl compounds (such as 1,3-bis-vinylsulfonyl-2-propanol, 1,2-bis(vinylsulfonylacetamido)ethane, bis(vinylsulfonylmethyl) ether and vinyl polymers having vinylsulfonyl groups at their side chains) are preferable because they rapidly harden the hydrophilic colloids such as gelatin to give stable photographic characteristics. N-Carbamoylpyridinium salts (such as (1-morpholinocarbonyl-3-pyridinio)methanesulfonate) and haloamidinium salts (such as 1-(1-chloro-1-pyridinomethylene)pyrrolizinium and 2-naphthalene sulfonate) shows an excellent properties in a high hardening rate.

The silver halide photographic emulsions used in the present invention may be spectrally sensitized with methine dyes or the like. Dyes used for spectral sensitization include cyanine dyes, merocyanine dyes, complex cyanine dyes, complex merocyanine dyes, holopolar cyanine dyes, hemicyanine dyes, styryl dyes and hemioxonol dyes. In particular, dyes belonging to the cyanine dyes, the merocyanine dyes and the complex merocyanine dyes are useful. Any nucleus usually employed in the cyanine dyes as a basic heterocyclic nucleus can be applied to these dyes. Such dyes include pyrroline, oxazoline, thiazoline, pyrrole, oxazole, thiazole, selenazole, imidazole, tetrazole and pyridine nuclei; nuclei in which alicyclic hydrocarbon rings are fused together with these nuclei; nuclei in which aromatic hydrocarbon rings are fused together with these nuclei, such as indolenine, benzindolenine, indole, benzoxazole, naphthoxazole, benzothiazole, naphthothiazole, benzoselenazole, benzimidazole and quinoline nuclei. These nuclei may be substituent groups at this carbon atoms.

Five-membered or 6-membered heterocyclic nuclei such as pyrazoline-5-one, thiohydantoin, 2-thiooxazolidine-2,4-dione, thiazolidine-2,4-dione, rhodanine and thiobarbituric acid nuclei may be applied to the merocyanine dyes or the complex merocyanine dyes as nuclei having a ketomethylene structure.

These sensitizing dyes may be used solely or in combination. In particular, they are frequently used in combination for supersensitization. The emulsions may contain dyes which themselves have no spectral sensitization action, or substances which do not substantially absorb visible light and exhibit supersensitization, as well as the sensitizing dyes. For example, the emulsions may contain aminostilbene compounds substituted with nitrogen-containing heterocyclic nucleus groups (for example, described in U.S. Pat. Nos. 2,933,390 and 3,635,721), aromatic organic acid-formaldehyde condensation products (for example, described in U.S. Pat. No. 3,743,510), cadmium salts and azaindene compounds. The combinations of the sensitizing dyes described in U.S. Pat. Nos. 3,615,613, 3,615,641, 3,617,295 and 3,635,721 are particularly useful.

The silver halide photographic emulsions of the present invention may contain various compounds to prevent fogging during manufacturing stages, storage or photographic processing of the light-sensitive materials or to stabilize photographic properties thereof. Namely, many compounds known as antifoggants or stabilizers can be added. Examples of such compounds include: azoles (such as benzothiazolium salts), nitroindazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles and mercaptotetrazoles (particularly, 1-phenyl-5-mercaptotetrazole); mercaptopyrimidines; mercaptotriazines; thioketo compounds (such as oxazoline-thione); azaindenes (such as triazaindenes, tetraazaindenes (particularly, 4-hydroxy-substituted (1,3,3a,7)tetraazaindenes) and pentaazaindenes); benzenethiosulfonic acid; benzenesulfinic acid; and benzenesulfonic acid amide.

The photographic material of the present invention may contain at least one surface active agent for various purposes such as coating assistance, the prevention of static charge, improvements in slippery properties, the promotion of emulsification and dispersing, the prevention of adhesion and improvements in photographic characteristics (for example, development acceleration, contrast enhancement and sensitization).

In the photographic materials of the present invention, the hydrophilic colloid layers may contain water-soluble dyes as filter dyes, for the purpose of preventing irradiation or halation or for various other purposes. Among theses dyes, oxonol dyes, hemioxonol dyes, styryl dyes, merocyanine dyes, anthraquinone dyes and azo dyes are preferred. In addition, cyanine dyes, azomethine dyes, triarylmethane dyes and phthalocyanine dyes are also useful. Oil-soluble dyes emulsified by oil-in-water dispersing methods can also be added to the hydrophilic colloid layers.

The present invention can be applied to a multi-layer, multi-color photographic material having at least two different sensitivities on a support. The multi-layer color photographic material usually has at least one layer for each of the red-sensitive, green-sensitive and blue-sensitive emulsion layers on the support. The order of arrangement of these layers can be arbitrarily selected as required. The preferred order of the layer arrangement is the red-sensitive layer, the green-sensitive layer and the blue-sensitive layer from the support side, the blue-sensitive layer, the green-sensitive layer and the red-sensitive layer, or the blue-sensitive layer, the red-sensitive layer and the green-sensitive layer. Any emulsion layers having the same color sensitivity may be each formed by at least two emulsion layers different in sensitivity to improve the resulting sensitivity, or may be formed in a three-layer structure to improve the graininess even further. A nonsensitive layer may be interposed between two or more layers having the same color sensitivity. Between emulsion layers having the same color sensitivity, an emulsion layer having a different color sensitivity may be inserted. A reflecting layer of a finely divided silver halide or the like may be provided under a high-sensitive layer, particularly under a high-sensitive blue-sensitive layer, to improve the sensitivity.

In general, the red-sensitive emulsion layer contains a cyan-forming coupler, the green-sensitive emulsion layer contains a magenta-forming coupler, and the blue-sensitive emulsion layer contains a yellow-forming coupler. However, different combinations may also be used if circumstances require. For example, the red-sensitive layers may be combined to use for pseudo-color photographs or semiconductor laser exposure.

Various color couplers may be used in the photographic materials of the present invention. Specific examples thereof are described in the patents cited in *Research Disclosure (RD)* No. 17643, VII-C to G.

Preferred examples of yellow couplers are described in U.S. Pat. Nos. 3,933,501, 4,022,620, 4,326,024 and 4,401,752, JP-B-58-10739, British Patents 1,425,020 and 1,476,760.

Among the magenta couplers, 5-pyrazolone compounds or pyrazoloazole compounds are preferred. Preferred examples thereof are described in U.S. Pat. Nos. 4,310,619 and 4,351,897, European Patent 73,636, U.S. Pat. Nos. 3,061,432 and 3,725,067, *Research Disclosure* No. 24220 (June 1984), JP-A-60-33552, *Research Disclosure* No. 24230 (June 1984), JP-A-60-43659, U.S. Pat. Nos. 4,500,630 and 4,540,654.

Cyan couplers include phenol couplers and naphthol couplers. Preferred examples thereof are described in U.S. Pat. Nos. 4,052,212, 4,146,396, 4,228,233, 4,296,200, 2,369,929, 2,801,171, 2,772,162, 2,859,826, 3,772,002, 3,758,308, 4,334,011 and 4,327,173, West German Patent (OLS) 3,329,729, European Patent 121,365A, U.S. Pat. Nos. 3,446,622, 4,333,999, 4,451,559 and 4,427,767, and European Patent 161,626A.

Preferred examples of colored couplers for correcting unnecessary absorption of forming dyes are described in *Research Disclosure* No. 17643, Item VII-G, U.S. Pat. No. 4,163,670, JP-B-57-39413, U.S. Pat. Nos. 4,004,929 and 4,138,258, and British Patent 1,146,368.

As couplers which provide forming dyes having appropriate diffusibility, for example, those described in U.S. Pat. No. 4,366,237, British Patent 2,125,570, European Patent 96,570 and West German Patent (OLS) 3,234,533 are preferable.

Typical examples of polymerized dye-forming couplers are described in U.S. Pat. Nos. 3,451,820, 4,080,211 and 4,367,282 and British Patent 2,102,173.

Couplers which release photographically useful residues upon coupling are also preferred. Preferred DIR couplers which release development inhibitors are described in the patents cited in the above-described RD 17643, Item VII-F, JP-A-57-151944, JP-A-57-154234, JP-A-60-184248 and U.S. Pat. No. 4,248,962.

Preferred couplers which release nucleating agents or development accelerators in image-like forms are described in British Patents 2,097,140 and 2,131,188, JP-A-59-157638 and JP-A-59-170840.

Other couplers which can be used in the photographic materials of the present invention include, for example, competitive couplers described in U.S. Pat. No. 4,130,427, multiequivalent couplers described in U.S. Pat. Nos. 4,283,472, 4,338,393 and 4,310, 618, DIR redox compound or DIR coupler releasing couplers described in JP-A-60-185950 and JP-A-62-24252, couplers which release dyes recoloring after elimination described in European Patent 173,302A, bleaching promoter releasing couplers described in RD No. 11449, ibid. No. 24241 and JP-A-61-201247, ligand releasing couplers described in U.S. Pat. No. 4,553,477.

The couplers used in the present invention can be incorporated in the photographic materials by various conventional dispersing methods.

Examples of high boiling solvents used in oil-in-water dispersion methods are described in U.S. Pat. No. 2,322,027.

Specific examples of the high boiling solvents which are used in the oil-in-water dispersion methods and have a boiling point of 175° C. or more at atmospheric pressure include: phthalates (for example, dibutyl phthalate, dicyclohexyl phthalate, di-2-ethylhexyl phthalate, decyl phthalate, bis(2,4-di-t-amylphenyl) phthalate, bis(2,4-di-t-amylphenyl) isophthalate and bis(1,1-diethylpropyl) phthalate), phosphates or phosphonates (for example, triphenyl phosphate, tricresyl phosphate, 2-ethylhexyldiphenyl phosphate, tricyclohexyl phosphate, tri-2-ethylhexyl phosphate, tridodecyl phosphate, tributoxyethyl phosphate, trichloropropyl phosphate and di-2-ethylhexylphenyl phosphonate), benzoates (for example, 2-ethylhexyl benzoate, dodecyl benzoate and 2-ethylhexyl-p-hydroxy benzoate), amides (for example, N,N-diethyldodecaneamide, N,N-diethyllaurylamide and N-tetradecylpyrrolidone), alcohols or phenols (for example, isostearyl alcohol and 2,4-di-tert-amylphenol), aliphatic carboxylic acid esters (for example, bis(2-ethylhexyl) sebacate, dioctyl azelate, glycerol tributyrate, isostearyl lactate and trioctyl citrate), aniline derivatives (for example, N,N-dibutyl-2-butoxy-5-tert-octylaniline), hydrocarbons (for example, paraffin, dodecylbenzene and diisopropylnaphthalene). Organic solvents having a boiling point of about 30° C. or more, preferably 50° to about 160° C. may be used as supplementary solvents. Typical examples thereof include ethyl acetate, butyl acetate, ethyl propionate, methyl ethyl ketone, cyclohexanone, 2-ethoxyethyl acetate and dimethylformamide.

The stages and effects of latex dispersion methods and specific examples of latexes for impregnation are described in U.S. Pat. No. 4,199,363, West German Patents (OLS) 2,541,274 and 2,541,230.

In the photographic materials of the present invention, the photographic emulsion layers and other layers are coated on a flexible support usually employed such as a plastic film, paper or cloth, or a rigid support such as a glass, a ceramic or a metal support. Useful flexible supports include films formed of semisynthetic or synthetic polymers such as cellulose nitrate, cellulose acetate, cellulose acetate butyrate, polystyrene, polyvinyl chloride, polyethylene terephthalate and polycarbonates, and paper coated or laminated with a baryta layer or an α-olefin polymer (for example, polyethylene, polypropylene or an ethylene-butene copolymer). The supports may be colored by dyes or pigments. They may be colored black to shield the light. In order to improve adhesion with the photographic emulsion layers or the like, the surface of the support is generally provided with an underlayer. The surface of the support may be subjected to glow discharge treatment, corona discharge treatment, ultraviolet irradiation treatment or flame treatment, before or after formation of the underlayer.

Various known coating methods such as a dip coating method, a roller coating method, a curtain coating method and an extrusion coating method can be utilized for the coating of the photographic emulsion layers and other hydrophilic colloid layers. Multiplelayers may be simultaneously formed by coating methods described in U.S. Pat. Nos. 2,681,294, 2,761,791, 3,526,528 and 3,508,947, as required.

The present invention can be applied to various color photographic materials and black-and-white materials. Typical examples thereof include negative color films for movies, reversal color films for slides or for television, color paper, color positive films, color reversal paper, color diffusion transfer photographic materials and thermal developing type color photographic materials. The present invention can also be applied to black-and-white materials such as photographic materials for X-ray photography by employing mixtures of three color couplers described in *Research Disclosure*, No. 17123 (July, 1978) or black color developing couplers described in U.S. Pat. No. 4,126,461 and British Patent 2,102,136. The present invention can also be applied to films for plate making such as lithographic films and scanner films, direct or indirect medical or industrial X-ray films, negative black-and-white films, black-and-white photographic paper, COM or normal microfilms, silver salt diffusion transfer photographic materials and print-out type photographic materials.

When the photographic materials of the present invention are applied to the color diffusion transfer photographic method, film units of a peel-apart type, an integrated type as described in JP-B-46-16356, JP-B-48-33697, JP-A-50-13040 and British Patent 1,330,524, or a peel-out unnecessary type as described in JP-A-57-119345, can be formed.

In the format of any of the above types, the use of a polymer acid layer protected by a neutralizing timing layer is advantageous to widen the permissible limit of the processing temperature. Also when used in the color diffusion transfer photographic method, the photographic material may be added to any layer of the sensitive material, or may be enclosed in a container for the processing solution as a component of the developing solution.

The photographic materials of the present invention can be exposed by various means. Any light source emitting the radiation corresponding to the light-sensitive wavelengths of the photographic materials can be used as illuminating light source or a write-in light source. Natural light (sun light), an incandescent lamp, a halogen atom-enclosed lamp, a mercury lamp, a fluorescent lamp and a flash light source such as an electronic flash or a metal burning flush valve are generally used. A gas, a dye solution, a semiconductor laser, a light emitting diode and a plasma light source which emit light in the wavelength range extending from the ultraviolet region to the infrared region can also be used. Further, fluorescence emitted from a fluorescent material excited with electron beams or the like (for example, CRT), and exposure means in which a linear or plane light source is combined with microshutter arrays utilizing lead titanium zirconate (PLZT) doping a liquid crystal display (LCD) or lanthanum, can also be used. The spectral distribution used for exposure is adjustable with color filters if necessary.

Color developing solutions for processing the photographic materials of the present invention are preferably an aqueous alkaline solutions mainly containing aromatic primary amine color developing agents. Although aminophenol compounds are also useful as the color developing agents, p-phenylenediamine compounds are preferably used. Typical examples thereof include: 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, and 3-methyl-4-amino-N-ethyl-N-β-methoxyethylaniline, as well as sulfates, hydrochlorides and p-toluenesulfonates thereof. These diamines are preferably used in the form of salts, because they are generally more stable in that form than in the free state.

Color developing solutions generally contain pH buffers such as alkali metal carbonates, borates and phosphates, and developing inhibitors or antifoggants such as bromides, iodides, benzimidazoles, benzothiazoles and mercapto compounds. Further, the color developing solutions may contain various preservatives such as hydroxylamines and sulfites, organic solvents such as triethanolamine and diethylene glycol, development accelerators such as benzyl alcohol, polyethylene glycol, quaternary ammonium salts and amines, dye forming couplers, competitive couplers, nucleating agents such as sodium boron hydride, auxiliary developing agents such as 1-phenyl-3-pyrazolidone, tackifiers, various chelating agents represented by aminopolycarboxylic acids, aminopolyphosphonic acids, alkylphosphonic acids and phosphonocarboxylic acids, and antioxidants described in German Patent Application (OLS) 2,622,950, as required.

In the processing of reversal color photographic materials, color development is usually conducted after black-and-white development. Black-and-white developing solutions used here may contain known black-and-white developing agents such as dihydroxybenzenes (for example, hydroquinone), 3-pyrazolidones (for example, 1-phenyl-3-pyrazolidone) and aminophenols (for example, N-methyl-p-aminophenol). These developing agents may be used separately or in combination.

After color development, the photographic emulsion layers are generally bleached. Bleaching may be carried out simultaneously with fixing or separately. Further, bleaching-fixing treatment may be conducted after bleaching to expedite processing. As bleaching agents, for example, compounds of polyvalent metals such as iron (III), cobalt (III), chromium (IV) and copper (II), peracids, quinones and nitrone compounds are used. Typical examples of the bleaching agents include: ferricyanides; bichromates; organic complex salts of iron (III) or cobalt (III), for example, complex salts of iron (III) or cobalt (III) with aminopolycarboxylic acids such as ethylenediaminetetraacetic acid, diethylenetriaminepentaacetic acid, nitrilotriacetic acid and 1,3-diamino-2-propanoltetraacetic acid, or with organic acids such as citric acid, tartaric acid and maleic acid; persulfates; manganates; and nitrosophenol. Of these, the salt of iron (III) with ethylenediaminetetraacetic acid, the salt of iron (III) with diethylenetriaminepentaacetic acid and persulfates are preferable from the viewpoints of rapid processing and environmental pollution. Further, the complex salt of iron (III) with ethylenediaminetetraacetic acid is also particularly useful for both independent bleaching solutions and combined bleaching-fixing solutions.

Bleaching promoters may be added to the bleaching solutions, the bleaching-fixing solutions and the preceding baths thereof, as required. Specific examples of the useful bleaching promoters include compounds having mercapto groups or disulfide groups described in U.S. Pat. No. 3,893,858, West German Patents 1,290,812 and 2,059,988, JP-A-53-32736, JP-A-53-57831, JP-A-53-37418, JP-A-53-65732, JP-A-53-72623, JP-A-53-95630, JP-A-53-95631, JP-A-53-104232, JP-A-53-124424, JP-A-53-141623, JP-A-53-28426 and *Research Disclosure*, No. 17129 (July, 1978); thiazolidine derivatives described in JP-A-50-140129; thiourea derivatives described in JP-B-45-8506, JP-A-52-20832, JP-A-53-32735 and U.S. Pat. No. 3,706,561; iodides described in West German Patent 1,127715 and JP-A-58-16235; polyethylene oxides described in West German Patents 966,410 and 2,748,430; polyamine compounds described in JP-B-45-8836; other compounds described in JP-A-49-42434, JP-A-49-59644, JP-A-53-94927, JP-A-54-35727, JP-A-55-26506 and JP-A-58-163940; and iodine and bromine ions. In particular, the compounds having mercapto groups or disulfide groups are preferable from the viewpoint of a high promoting effect, and the compounds described in U.S. Pat. No. 3,893,858, West German Patent 1,290812 and JP-A-53-95630 are particularl preferable. In addition, the compounds described in U.S. Pat. No. 4,552,834 are also preferable. These bleaching promoters may be added to the photographic materials. When color photographic materials for shooting are subjected to the bleaching-fixing, these bleaching promoters are particularly effective.

Fixing agents include thiosulfates, thiocyanates, thioether compounds and large quantities of iodides. The thiosulfates are generally used. As preservatives for the bleaching-fixing solutions or the fixing solutions, sulfites, bisulfites or carbonyl bisulfite addition compounds are preferably used.

The photographic materials are usually subjected to washing and stabilizing stages after bleaching-fixing or fixing. In the washing and stabilizing stages, various known compounds may be added to prevent precipitation or to save water. For example, in order to prevent precipitation, various compounds can be added as required, including water softeners such as inorganic phosphoric acids, aminopolycarboxylic acids, organic aminopolyphosphonic acids and organic phosphoric acids; disinfectants or antifungal agents for preventing various bacteria, duckweeds or molds from being produced; metal salts represented by magnesium salts, aluminum salts and bismuth salts; surface active agents for preventing the load and unevenness of drying; and various hardeners. Also, compounds described in L. E. West, *Phot. Sci. Enc.* vol. 6, pages 344 to 359 (1965) may be added. The addition of chelating agents or the antifungal agents is particularly effective.

In the washing stage, a countercurrent washing system using two or more tanks is usually employed to save water. Further, a multistage countercurrent stabilizing stage described in JP-A-57-8543 may be carried out instead of the washing stage. This stage requires 2 to 9 countercurrent baths. In addition to the above-described additives, various compounds are added to these stabilizing baths to stabilize images. Typical examples thereof include various buffers for adjusting the pH of films (for example, to pH 3 to 9) (for example, borates, metaborates, borax, phosphates, carbonates, potassium hydroxide, sodium hydroxide, aqueous ammonia, monocarboxylic acids, dicarboxylic acids and polycarboxylic acids are used in combination) and aldehydes such as formaldehyde. In addition, various additives may be used if necessary, and two or more compounds which are the same or different in their object may be used in combination. Such additives include chelating agents (such as inorganic phosphoric acids, aminopolycarboxylic acids, organic phosphoric acids, organic phosphonic acids, aminopolyphosphonic acids and phosphonocarboxylic acids), disinfectants (such as benzoisothiazolinone, isothiazolone, 4-thiazolinebenzimidazole halogenated phenol, sulfanilamide and benzotriazole), surface active agents, fluorescent brightening agents and hardeners.

After processing, various ammonium salts are preferably added as film pH adjusting agents. Such ammonium salts include ammonium chloride, ammonium nitrate, ammonium sulfate, ammonium phosphate, ammonium sulfite and ammonium thiosulfate.

With the color photographic materials for shooting, the washing-stabilizing stage usually carried out after fixing can also be replaced by the above-described stabilizing stage and washing stage (water saving treatment). In this case, when two equivalents of a magenta coupler are used, formaldehyde contained in the stabilizing bath may be removed.

In the present invention, the washing time and the stabilizing time are each usually 20 seconds to 10 minutes, and preferably 20 seconds to 5 minutes, though they vary depending on the kind of photographic material and the processing conditions.

The silver halide color photographic materials of the present invention may contain color developing agents in order to simplify and expedite processing. It is preferred to use various precursors of the color developing agents for this purpose. Examples of such precursors include indoaniline compounds described in U.S. Pat. No. 3,342,597, Schiff base type compounds described in U.S. Pat. No. 3,342,599, *Research Disclosure*, No. 14850 and ibid., No. 15159, aldol compounds described in *Research Disclosure*, No. 13924, metal salt complexes described in U.S. Pat. No. 3,719,492, urethane compounds described in JP-A-53-135628, and various salt type precursors described in JP-A-56-6235, JP-A-56-16133, JP-A-56-59232, JP-A-56-67842, JP-A-56-83734, JP-A-56-83735, JP-A-56-83436, JP-A-56-89735, JP-A-56-81837, JP-A-56-54430, JP-A-56-106241, JP-A-56-107236, JP-A-57-97531 and JP-A-57-83565.

The silver halide color photographic materials of the present invention may contain various 1-phenyl-3-pyrazolidones for the purpose of promoting color development, as required. Typical compounds thereof are described in JP-A-56-64339, JP-A-57-144547, JP-A-57-

211147, JP-A-58-50532, JP-A-58-50536, JP-A-58-50533, JP-A-58-50534, JP-A-58-50535 and JP-A-58-115438.

The processing solutions for the present invention are used at a temperature of 10° to 50° C. The standard temperature is usually 33° to 38° C. However, the temperature may be elevated higher to expedite processing, whereby the processing time can be shortened. On the contrary, the temperature can be decreased to achieve improvements in image qualities and in stability of the processing solutions. In addition, processing may be conducted using cobalt intensification or hydrogen peroxide intensification described in West German Patent 2,226,770 and U.S. Pat. No. 3,674,499 to save the silver of the photographic materials.

Various processing baths may be provided with heaters, temperature sensors, level sensors, circulating pumps, filters, floating covers and squeegees, if necessary.

In continuous processing a constant finish is obtained by preventing the fluctuation of the solution composition, using the replenisher of each processing solution. The replenishment rate can be reduced to one half or less of the standard replenishment rate for cost reduction.

When the photographic materials of the present invention are color paper, the bleaching-fixing processing can be generally carried out. Also when they are photographic materials for shooting, the bleaching-fixing processing can be conducted, as desired.

Specific examples of the present invention are shown below, which are not to be construed as limiting the scope thereof.

EXAMPLE 1

A silver nitrate solution and a mixed solution containing potassium iodide and potassium bromide were added to a solution in which potassium bromide, thioether $(HO(CH_2)_2S(CH_2)_2S(CH_2)_2OH)$ and gelatin were dissolved and which is maintained at 70° C., with stirring by the double jet method.

After completion of addition, the temperature of the resulting solution was reduced to 35° C., and soluble salts were removed by the conventional flocculation method. Then, the temperature was elevated to 40° C. again. In addition, 60 g of gelatin was added thereto and dissolved to adjust the pH to 6.8.

The resulting tabular silver halide grains had a mean diameter of 1.25 μm, a thickness of 0.17 μm and a mean diameter/thickness ratio of 7.4. The silver content was 3 mol %, and the pAg was 8.4 at 40° C.

After the emulsion was divided into 12 parts, the temperature thereof was elevated to 62° C. A sensitizing dye, the sodium salt of anhydro-5,5'-dichloro-9-ethyl-3,3'-di(3-sulfopropyl)oxacarbocyaninehydroxide (500 ng/mol of AgX) and potassium iodide (200 mg/mol of AgX) were added thereto, and further the sensitizers shown in Table 1 were each added to the divided emulsions. In addition, chloroauric acid ($9 \times 10^{-6}$ mol/mol of AgX) and potassium thiocyanate ($3.2 \times 10^{-4}$ mol/mol of AgX) were added, followed by chemical ripening for 30 minutes.

After completion of the chemical ripening, 100 g of each emulsion (containing 0.08 mol of Ag) was dissolved at 40° C., and the following compounds (1) to (4) were combined in turn with stirring to prepare a coating solution:

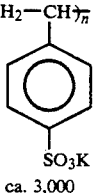

| | |
|---|---|
| (1) 4-Hydroxy-6-methyl-1,3,3a,7-tetraazaindene | 3% 2 cc; |
| (2) $C_{17}H_{35}$—O—$(CH_2CH_2O)_{25}$—H | 2% 2.2 cc; |
| (3) $+CH_2-CH\!\!\rightarrow_n$ <br> (phenyl-SO₃K) <br> n = ca. 3,000 | 2% 1.6 cc; and |
| (4) 2,4-Dichloro-6-hydroxy-S-triazine sodium | 2% 3 cc. |

The following compounds (1) to (5) were combined at 40° C. in turn with stirring to prepare a surface protective layer coating solution:

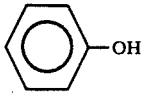

| | |
|---|---|
| (1) 14% Aqueous Solution of Gelatin | 56.8 g; |
| (2) Fine Grains of Polymethyl Methacrylate (mean grain size: 3.0 μm) | 3.9 g; |
| (3) Emulsion Gelatin | 10% 4.24 g, |
| $CH_2COOCH_2CH(C_2H_5)C_4H_9$ <br> $NaO_3S-CHCOOCH_2CH(C_2H_5)C_4H_9$ | 10.6 mg |
| (phenyl-OH) | 72% 0.02 cc |
| (silicone structure) | 0.424 g |
| (4) $H_2O$ | 68.8 cc, |

(5) 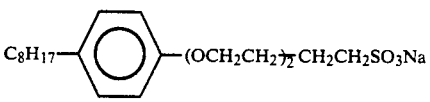 4.3% 3 cc.

A support of a polyethylene terephthalate film was coated with both the emulsion coating solution and the surface protective layer coating solution by a simultaneous extrusion method to give a volume ratio of 103:45 when coated. The amount of coated silver was 2.5 g/m². These samples were exposed (for 1/100 seconds) by a sensitometer through a yellow filter and an optical wedge, and then developed with an RD-III developing solution for automatic processors (manufactured by Fuji Photo Film Co., Ltd.) at 35° C. for 30 seconds, followed by fixing, washing and drying according to conventional methods. Then, the photographic sensitivity was measured. The photographic sensitivity was represented by the logarithm of the reciprocal of the exposure required to obtain an optical density of a fogging value +0.1, and the sensitivity of Sample 1 was taken as 100.

As is apparent from Table 1, compared to sulfur-gold sensitization, known selenium-gold sensitization or selenium-sulfur-gold sensitization using selenium compounds, is high in sensitivity, but there is much fogging. However, the use of the selenium sensitizers of the present invention provides sensitization low in fogging and having sensitivity to a similarly high degree, though it cannot reach to a level of the sulfur-gold sensitization in fogging.

TABLE 1

| Sample | Sensitizing Agent (added amount, mol/mol of silver) | Fogging | Relative Sensitivity | Relation to This Application |
|---|---|---|---|---|
| 1 | Sodium Thiosulfate ($1.8 \times 10^{-5}$) | 0.14 | 100 | Comparison |
| 2 | N,N-Dimethylselenourea*1 ($2 \times 10^{-6}$) | 0.36 | 132 | Comparison |
| 3 | N,N,N',N'-Tetramethylselenourea*2 ($10 \times 10^{-6}$) | 0.34 | 130 | Comparison |
| 4 | N,N-Dimethylselenourea ($1 \times 10^{-6}$) Sodium Thiosulfate ($8 \times 10^{-6}$) | 0.32 | 128 | Comparison |
| 5 | Example Compound I-1 ($4 \times 10^{-6}$) | 0.22 | 130 | Invention |
| 6 | Example Compound I-2 ($3 \times 10^{-6}$) | 0.23 | 130 | Invention |
| 7 | Example Compound I-14 ($2 \times 10^{-6}$) | 0.25 | 132 | Invention |
| 8 | Example Compound II-3 ($2 \times 10^{-6}$) | 0.28 | 132 | Invention |
| 9 | Example Compound II-4 ($2 \times 10^{-6}$) | 0.28 | 135 | Invention |
| 10 | Example Compound II-13 ($2 \times 10^{-6}$) | 0.26 | 135 | Invention |
| 11 | Example Compound I-1 ($2 \times 10^{-6}$) Sodium Thiosulfate ($8 \times 10^{-6}$) | 0.19 | 126 | Invention |
| 12 | Example Compound II-3 ($1 \times 10^{-6}$) Sodium Thiosulfate ($8 \times 10^{-6}$) | 0.20 | 128 | Invention |

Comparative compounds *1 and *2 shown in Table 1 are described in U.S. Pat. No. 3,297,447.

EXAMPLE 2

(Tabular Silver Iodobromide Grains)

Fine-Grain Silver Iodobromide Emulsion II-A

To 2.6 l of a 2.0 wt % gelatin solution containing 0.026 mol of potassium bromide, 1200 ml of a 1.2 mol silver nitrate solution and 1200 ml of an aqueous solution of halogen salts containing 1.11 mol of potassium bromide and 0.09 mol of potassium iodide were added with stirring for 15 minutes by a double jet method. The gelatin solution was maintained at 35° C. during this operation. Then, the emulsion was washed by a conventional flocculation method, and 30 g of gelatin was dissolved therein, followed by adjustment to pH 6.5 and pAg 8.6. The resulting fine silver iodobromide grains (the content of silver iodide: 7.5%) had a mean grain size of 0.07 μm.

Tabular Silver Bromide Core Emulsion II-B

To 2 l of a 0.8 wt % gelatin solution containing 0.09 mol of potassium bromide, 30 cc of a 2.0 mol silver nitrate solution and 30 cc of 2.0 mol potassium bromide solution were added with stirring by a double jet method. During this operation, the gelatin solution in the reaction vessel was maintained at 30° C. After addition, the temperature of the solution was elevated to 75° C., followed by addition of 40 g of gelatin. Then, 1.0 mol silver nitrate solution was added to adjust the pBr to 2.55. Subsequently, 150 g of silver nitrate was added thereto for 60 minutes at an accelerated flow rate so that the flow rate at the time when the addition was completed was increased to 10 times that at the time when the addition had started. At the same time, the potassium bromide solution was added so as to give a pBr of 2.55 by a double jet method.

Then, the emulsion was cooled to 35° C., and washed with water by a conventional flocculation method. Thereafter, 60 g of gelatin was added thereto and dissolved at 40° C., followed by adjustment to pH 6.5 and pAg 8.6. The resulting tabular silver bromide grains were tabular monodisperse grains having a mean circle-corresponding diameter of 1.4 μm, a grain thickness of 0.2 μm and a coefficient of variation in circle-corresponding diameter of 15%.

Tabular Silver Iodobromide Emulsion II-C

Emulsion II-B containing silver bromide in an amount corresponding to 50 g of silver nitrate was dissolved in 1.1 l of water, and the resulting solution was maintained at 75° C. at pBr of 1.5. Then, 1 g of 3,6-dithiaoctane-1,8- diol was added thereto, and immediately, fine grain emulsion II-A was added in the amount of 100 g in silver nitrate to a reaction vessel at a constant flow rate for 50 minutes. The resulting tabular grains had a mean circle-corresponding diameter of 2.4 m and a grain thickness of 0.31 μm.

Then, the emulsion was washed with water by a conventional flocculation method, and adjusted to pH 6.5 and pAg 8.6.

After the emulsion thus obtained was divided into 6 parts, the temperature thereof was elevated to 56° C. A sensitizing dye, the sodium salt of anhydro-5-chloro-5'-phenyl-9-ethyl-3,3'-di(3-sulfopropyl)oxacarbocyaninehydroxide was added thereto, and then the sensitizers shown in Table 2 were each added to the divided emulsions. Subsequently, chloroauric acid ($1 \times 10^{-5}$ mol/mol of AgX) and potassium thiocyanate ($6 \times 10^{-4}$ mol/mol of AgX) were added thereto, followed by optimum chemical ripening. Then, the following compounds were added thereto, and applied together with a protective layer to a support of a triacetyl cellulose film provided with an underlayer by the simultaneous extrusion method.

(1) Emulsion Layer

Emulsion: each emulsion Sample shown in Table 2

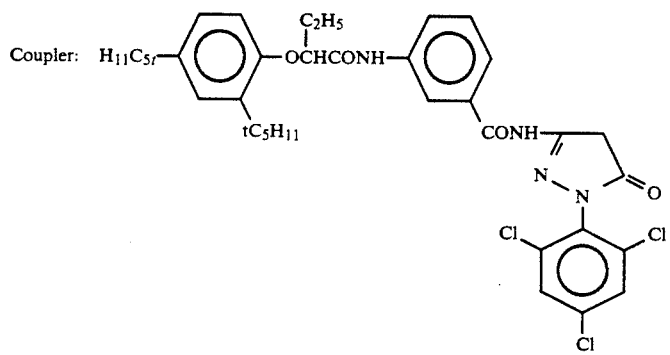

Coupler:

Tricresyl Phosphate
Stabilizer: 4-Hydroxy-6-methyl-1,3,3a,7-tetraazaindene
Coating Assistant: Sodium Dodecylbenzenesulfonate (2) Protective Layer Polymethyl Methacrylate Grains
Sodium Salt of 2,4-Dichloro-6-hydroxy-s-triazine
Gelatin These samples were subjected to exposure for sensitometry for 1/100 second, and the following color processing.

The density of the processed samples was measured through a green filter. The resulting photographic properties are shown in Table 2. For the relative sensitivity, that of Sample 13 was taken as 100.

The processing was conducted at 38° C. under the following conditions:

| 1. Color Development: | 2 min and 45 sec; |
|---|---|
| 2. Bleaching: | 6 min and 30 sec; |
| 3. Washing: | 3 min and 15 sec; |
| 4. Fixing: | 6 min and 30 sec; |
| 5. Washing: | 3 min and 15 sec; |
| 6. Stabilizing: | 3 min and 15 sec. |

The composition of processing solutions used in the respective stages was as follows:

| Color Developing Solution | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N-Ethyl-N-β-hydroxyethylamino)- | 4.5 g |

| -continued | |
|---|---|
| 2-methylaniline Sulfate | |
| Water to make | 1 l |
| Bleaching Solution | |
| Ammonium Bromide | 160.0 g |
| Aqueous Ammonia (28%) | 25.0 ml |
| Sodium Ethylenediaminetetraacetate | 130 g |
| Glacial Acetic Acid | 14 ml |
| Water to make | 1 l |
| Fixing Solution | |
| Sodium Tetrapolyphosphate | 2.0 g |
| Sodium Sulfite | 15 g |
| Ammonium Thiosulfate (70%) | 175 ml |
| Sodium Bisulfite | 4.6 g |
| Water to make | 1 l |
| Stabilizing Solution | |
| Formalin | 8.0 ml |
| Water to make | 1 l |

TABLE 2

| Sample | Sensitizing Agent (added amount, mol/mol of silver) | Fogging | Relative Sensitivity | Relation to This Application |
|---|---|---|---|---|
| 13 | Sodium Thiosulfate ($1.2 \times 10^{-5}$) | 0.28 | 100 | Comparison |
| 14 | N,N-Dimethylselenourea*[1] ($2 \times 10^{-6}$) | 0.65 | 126 | Comparison |
| 15 | Example Compound I-1 ($4 \times 10^{-6}$) | 0.34 | 122 | Invention |
| 16 | Example Compound I-2 ($3 \times 10^{-6}$) | 0.37 | 124 | Invention |
| 17 | Example Compound I-14 ($2 \times 10^{-6}$) | 0.39 | 124 | Invention |
| 18 | Example Compound II-3 ($2 \times 10^{-6}$) | 0.42 | 127 | Invention |

In this table, comparative compound *[1] is the same as that shown in Table 1.

As is apparent from Table 2, selenium sensitization using conventional compounds is high in sensitivity, but remarkably high in the generation of fogging particularly in color development. However, the use of the selenium sensitizers of the present invention can give the effects that the fogging is significantly depressed and a similar high degree of sensitivity is obtained.

EXAMPLE 3

Preparation of Em-H

One thousand ml of an aqueous solution containing 10.5 g of gelatin and 3 g of KBr was stirred at 60° C., and an aqueous solution of AgNO$_3$ (8.2 g) and an aqueous solution of KBr (containing 5.7 g of KBr and 0.35 g of KI) were added thereto by a double jet method. Gelatin was added thereto and the temperature was elevated to 75° C. After the potential was adjusted to 0 mV, an aqueous solution of AgNO$_3$ (136.3 g) and an aqueous solution of KBr (containing 12.0 mol % of KI) were added by the double jet method. At this time, the silver potential was maintained at 0 mV to a saturated calomel electrode. After the silver potential was adjusted to −60 mV, the temperature was lowered to 40° C., and an aqueous solution of AgNO$_3$ (3.2 g) and an aqueous solution of KI (2.3 g) were added for 5 minutes. K$_3$IrCl$_6$ was added thereto in an amount of 7.0×10$^{-7}$ mol/mol of Ag, and then an aqueous solution of AgNO$_3$ (22.3 g) and an aqueous solution of KBr were added thereto for 5.35 minutes by the double jet method. At this time, the silver potential was maintained at −100 mV to the saturated calomel electrode.

Twenty ml of 0.1 N potassium thiocyanate was added, followed by desalting according to a flocculation method. Gelatin was added to the emulsion, which was adjusted to pH 5.5 and pAg 8.2. The resulting emulsion had tabular grains having a mean circle-corresponding diameter of 1.42 μm, a mean thickness of 0.21 μm and a mean aspect ratio of 6.8. The coefficient of variation in circle-corresponding diameter was 15%.

Em-H was subjected to gold-sulfur-selenium sensitization in the following manner. The temperature of each emulsion was elevated to 72° C., and to each emulsion were added 3.3×10$^{-4}$ mol/mol of Ag of the following sensitizing dye Dye-5, 3.2×10$^{-4}$ mol/mol of Ag of the following sensitizing dye Dye-6, 1.7×10$^{-5}$ mol/mol of Ag of the following sensitizing dye Dye-7, 1×10$^{-4}$ mol/mol of Ag of antifoggant V-I shown in Table A, 2.3×10$^{-6}$ mol/mol of Ag of sodium thiosulfate, 9.2×10$^{-6}$ mol/mol of Ag of chloroauric acid, 3.0×10$^{-3}$ mol/mol of Ag of potassium thiocyanate and each sensitizer shown in Table 3, followed by optimum chemical sensitization. The term "optimum chemical sensitization" means chemical sensitization so that the highest sensitivity is obtained when the exposure is made for 1/100 seconds after the chemical sensitization.

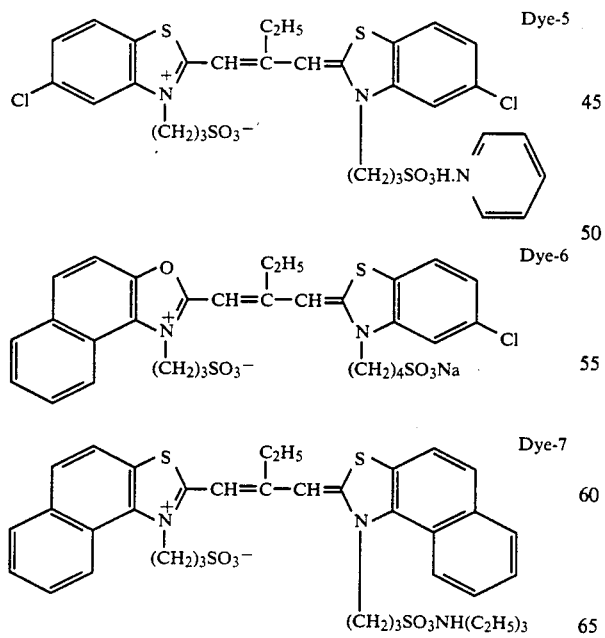

A support of a cellulose triacetate film provided with a subbing was coated with the respective layers having the following composition to prepare multilayer color photographic materials, i.e., Samples 19 to 24.

Composition of Light-Sensitive Layers

The figure corresponding to each component indicates the coated amount represented by g/m$^2$. For silver halides, it indicates the coated amount converted to the amount of silver. However, for sensitizing dyes, the coated amount per mol of silver halide contained in the same layer is indicated by mol. Structures of various addition compounds are shown in Table A.

| First Layer: Antihalation Layer | |
|---|---|
| Black Colloidal Silver silver | 0.18 |
| Gelatin | 1.40 |
| Second Layer: Intermediate Layer | |
| 2,5-Di-t-pentadecylhydroquinone | 0.18 |
| EX-1 | 0.07 |
| EX-3 | 0.02 |
| EX-12 | 0.002 |
| U-1 | 0.06 |
| U-2 | 0.08 |
| U-3 | 0.10 |
| HBS-1 | 0.10 |
| HBS-2 | 0.02 |
| Gelatin | 1.04 |
| Third Layer: Multilayer Effective Donor Layer to Red-Sensitive Layer | |
| Emulsion 9 silver | 1.2 |
| Emulsion 10 silver | 2.0 |
| Sensitizing Dye IV | 4 × 10$^{-4}$ |
| EX-10 | 0.10 |
| HBS-1 | 0.10 |
| HBS-2 | 0.10 |
| Gelatin | 2.82 |
| Fourth Layer: Intermediate Layer | |
| EX-5 | 0.040 |
| HBS-1 | 0.020 |
| Gelatin | 0.80 |
| Fifth Layer: First Red-Sensitive Emulsion Layer | |
| Emulsion 1 silver | 0.25 |
| Emulsion 2 silver | 0.25 |
| Sensitizing Dye I | 1.5 × 10$^{-4}$ |
| Sensitizing Dye II | 1.8 × 10$^{-5}$ |
| Sensitizing Dye III | 2.5 × 10$^{-4}$ |
| EX-2 | 0.335 |
| EX-10 | 0.020 |
| U-1 | 0.07 |
| U-2 | 0.05 |
| U-3 | 0.07 |
| HBS-1 | 0.060 |
| Gelatin | 0.87 |
| Sixth Layer: Second Red-Sensitive Emulsion Layer | |
| Emulsion 6 silver | 1.0 |
| Sensitizing Dye I | 1.0 × 10$^{-4}$ |
| Sensitizing Dye II | 1.4 × 10$^{-5}$ |
| Sensitizing Dye III | 2.0 × 10$^{-4}$ |
| EX-2 | 0.400 |
| EX-3 | 0.050 |
| EX-10 | 0.015 |
| U-1 | 0.07 |
| U-2 | 0.05 |
| U-3 | 0.07 |
| Gelatin | 1.30 |
| Seventh Layer: Third Red-Sensitive Emulsion Layer | |
| Em-H silver | 1.60 |
| EX-3 | 0.010 |
| EX-4 | 0.080 |
| EX-2 | 0.097 |
| EX-8 | 0.080 |
| HBS-1 | 0.22 |
| HBS-2 | 0.10 |
| Gelatin | 1.63 |
| Eighth Layer: Intermediate Layer | |
| Ex-5 | 0.040 |
| HBS-1 | 0.020 |
| Gelatin | 0.80 |
| Ninth Layer: First Green-Sensitive Emulsion Layer | |

-continued

| | |
|---|---|
| Emulsion 1 silver | 0.15 |
| Emulsion 2 silver | 0.15 |
| Sensitizing Dye V | $3.0 \times 10^{-5}$ |
| Sensitizing Dye VI | $1.0 \times 10^{-4}$ |
| Sensitizing Dye VII | $3.8 \times 10^{-4}$ |
| Sensitizing Dye IV | $5.0 \times 10^{-5}$ |
| EX-6 | 0.260 |
| EX-1 | 0.021 |
| EX-7 | 0.030 |
| EX-8 | 0.005 |
| HBS-1 | 0.100 |
| HBS-3 | 0.010 |
| Gelatin | 0.63 |
| Tenth Layer: Second Green-Sensitive Emulsion Layer | |
| Emulsion 3 silver | 0.45 |
| Sensitizing Dye V | $2.1 \times 10^{-5}$ |
| Sensitizing Dye VI | $7.0 \times 10^{-5}$ |
| Sensitizing Dye VII | $2.6 \times 10^{-4}$ |
| Sensitizing Dye IV | $5.0 \times 10^{-5}$ |
| EX-6 | 0.094 |
| EX-22 | 0.018 |
| EX-7 | 0.026 |
| HBS-1 | 0.160 |
| HBS-3 | 0.008 |
| Gelatin | 0.50 |
| Eleventh Layer: Third Green-Sensitive Emulsion Layer | |
| Emulsion 4 silver | 1.2 |
| Sensitizing Dye V | $3.5 \times 10^{-5}$ |
| Sensitizing Dye VI | $8.0 \times 10^{-5}$ |
| Sensitizing Dye VII | $3.0 \times 10^{-4}$ |
| Sensitizing Dye IV | $0.5 \times 10^{-5}$ |
| EX-13 | 0.015 |
| EX-11 | 0.100 |
| EX-1 | 0.025 |
| HBS-1 | 0.25 |
| HBS-2 | 0.10 |
| Gelatin | 1.54 |
| Twelfth Layer: Yellow Filter Layer | |
| Yellow Colloidal Silver silver | 0.05 |
| EX-5 | 0.08 |
| HBS-1 | 0.03 |
| Gelatin | 0.95 |
| Thirteenth Layer: First Blue-Sensitive Emulsion Layer | |
| Emulsion 1 silver | 0.08 |
| Emulsion 2 silver | 0.07 |
| Emulsion 5 silver | 0.07 |
| Sensitizing Dye VIII | $3.5 \times 10^{-4}$ |
| EX-9 | 0.721 |
| EX-8 | 0.042 |
| HBS-1 | 0.28 |
| Gelatin | 1.10 |
| Fourteenth Layer: Second Blue-Sensitive Emulsion Layer | |
| Emulsion 6 silver | 0.45 |
| Sensitizing Dye VIII | $2.1 \times 10^{-4}$ |
| EX-9 | 0.154 |
| EX-10 | 0.007 |
| HBS-1 | 0.05 |
| Gelatin | 0.78 |
| Fifteenth Layer: Third Blue-Sensitive Emulsion Layer | |
| Emulsion 7 silver | 0.77 |
| Sensitizing Dye VIII | $2.2 \times 10^{-4}$ |
| EX-9 | 0.20 |
| HBS-1 | 0.07 |
| Gelatin | 0.69 |
| Sixteenth Layer: First Protective Layer | |
| Emulsion 8 silver | 0.20 |
| U-4 | 0.11 |
| U-5 | 0.17 |
| HBS-1 | 0.05 |
| Gelatin | 1.00 |
| Seventeenth Layer: Second Protective Layer | |
| Polymethyl Methacrylate Particles (diameter: about 1.5 μm) | 0.54 |
| S-1 | 0.20 |
| Gelatin | 1.20 |

In addition to the above-described components, at least one of gelatin hardeners H-1 and EX-14 to EX-21 and/or a surface active agent are added to each layer.

| | Mean AgI Content (%) | Mean Grain Size (μm) | Coefficient of Variation of Grains (%) | Diameter/Thickness Ratio |
|---|---|---|---|---|
| Emulsion 1 | 4.0 | 0.45 | 27 | 1 |
| Emulsion 2 | 8.9 | 0.70 | 14 | 1 |
| Emulsion 3 | 10 | 0.75 | 30 | 2 |
| Emulsion 4 | 10 | 1.05 | 35 | 3 |
| Emulsion 5 | 4.0 | 0.25 | 28 | 1 |
| Emulsion 6 | 14.0 | 0.75 | 25 | 2 |
| Emulsion 7 | 14.5 | 1.30 | 25 | 3 |
| Emulsion 8 | 1 | 0.07 | 15 | 1 |
| Emulsion 9 | 5 | 0.90 | 30 | 2 |
| Emulsion 10 | 7 | 1.50 | 25 | 2 |

| | Silver Amount Ratio (AgI content %) |
|---|---|
| Emulsion 1 | Core/shell = 1/3 (13/1), double structural grain |
| Emulsion 2 | Core/shell = 3/7 (25/2), double structural grain |
| Emulsion 3 | Core/shell = 1/2 (24/3), double structural grain |
| Emulsion 4 | Core/shell = 1/2 (24/3), double structural grain |
| Emulsion 5 | Core/shell = 1/3 (13/1), double structural grain |
| Emulsion 6 | Core/shell = 1/2 (42/0), double structural grain |
| Emulsion 7 | Core/shell = 37/63 (34/3), double structural grain |
| Emulsion 8 | Uniform grain |
| Emulsion 9 | Core/shell = 1/1 (10/0), double structural grain |
| Emulsion 10 | Core/shell = 1/1 (14/0), double structural grain |

Color photographic materials 19 to 26 obtained as described above were exposed, and then processed using the following processing stages in an automatic processor until the accumulated replenishment rate of the bleaching solution amounted to three times its mother liquor tank.

| Processing Stages | | | | |
|---|---|---|---|---|
| | Processing Time | Processing Temperature (°C.) | Replenishment Rate (ml) | Tank Capacity (l) |
| Color Development | 3 min and 15 sec | 38 | 15 | 20 |
| Bleaching | 6 min and 30 sec | 38 | 10 | 40 |
| Rinsing | 2 min and 10 sec | 35 | 10 | 20 |
| Fixing | 4 min and 20 sec | 38 | 20 | 30 |
| Rinsing (1) | 1 min and 05 sec | 35 | Countercurrent piping system from (2) to (1) | 10 |
| Rinsing (2) | 1 min and 00 sec | 35 | 20 | 10 |
| Stabilizing | 1 min and 05 sec | 38 | 10 | 10 |
| Drying | 4 min and 20 min | 55 | | |

The replenishment rate is indicated by an amount per 35 mm in width by 1 m in length.

The composition of the processing solutions was as follows:

| | Mother Liquor (g) | Replenisher (g) |
|---|---|---|
| Color Developing Solution | | |
| Diethylenetriaminetetraacetic Acid | 1.0 | 1.1 |
| 1-Hydroxyethylidene-1,1-diphosphonic Acid | 3.0 | 3.2 |
| Sodium Sulfite | 4.0 | 4.9 |
| Potassium Carbonate | 30.0 | 30.0 |
| Potassium Bromide | 1.4 | — |
| Potassium Iodide | 1.5 mg | |

|  | Mother Liquor (g) | Replenisher (g) |
|---|---|---|
| Hydroxylamine Sulfate | 2.4 | 3.6 |
| 4-(N-Ethyl-N-$\beta$-hydroxyethylamino)-2-methylaniline Sulfate | 4.5 | 7.2 |
| Water to make | 1.0 l | 1.0 l |
| pH | 10.05 | 10.10 |
| Bleaching Solution | | |
| Fe (III) Sodium Ethylenediamine-tetraacetate Trihydrate | 100.0 | 140.0 |
| Disodium Ethylenediaminetetraacetate | 10.0 | 11.0 |
| Ammonium Bromide | 140.0 | 180.0 |
| Ammonium Nitrate | 30.0 | 40.0 |
| Aqueous Ammonia (27%) | 6.5 ml | 2.5 ml |
| Water to make | 1.0 l | 1.0 l |
| pH | 6.0 | 5.5 |
| Fixing Solution | | |
| Disodium Ethylenediaminetetraacetate | 0.5 | 1.0 |
| Sodium Sulfite | 7.0 | 12.0 |
| Sodium Bisulfite | 5.0 | 9.5 |
| Aqueous Ammonium Thiosulfate (70%) | 170.0 ml | 240.0 ml |
| Water to make | 1.0 l | 1.0 l |
| pH | 6.7 | 6.5 |
| Rinsing Solution (mother liquor and replenisher being the same) | | |

Tap water was passed through a mixed bed column filled with an H-type strongly acidic cation exchange resin (Amberlite IR-120B manufactured by Rohm & Haas Co.) and an OH-type anion exchange resin (Amberlite IR-400 manufactured by Rohm & Haas Co.) to reduce the ion concentrations of calcium and magnesium to 3 mg or less, and subsequently, 20 mg/l of sodium isocyanurate dichloride and 1.5 g/l of sodium sulfate were added thereto.

The pH of this solution was within the range of 6.5 to 7.5.

| Fixing Solution | Mother Liquor (g) | Replenisher (g) |
|---|---|---|
| Formaldehyde (37%) | 2.0 ml | 3.0 ml |
| Polyoxyethylene-p-monononylphenyl-ether (average degree of polymerization: 10) | 0.3 | 0.45 |
| Disodium Ethylenediaminetetra-acetate | 0.05 | 0.08 |
| Water to make | 1.0 l | 1.0 l |
| pH | 5.0–8.0 | 5.0–8.0 |

With respect to the characteristic curves of cyan color images, sensitivity was indicated by the fogging density and the relative value of the reciprocal of the exposure which gives a density 0.1 higher than the fogging density. The results obtained are shown in Table 3.

TABLE 3

| Sample | Sensitizing Agent (added amount, mol/mol of Ag) | Fogging | Relative Sensitivity | Relation to This Application |
|---|---|---|---|---|
| 19 | N,N-Dimethylselenourea*1 ($2 \times 10^{-6}$) | 0.18 | 100 | Comparison |
| 20 | Example Compound I-1 ($4 \times 10^{-6}$) | 0.10 | 100 | Invention |
| 21 | Example Compound I-2 ($3 \times 10^{-6}$) | 0.08 | 102 | Invention |
| 22 | Example Compound I-14 ($3 \times 10^{-6}$) | 0.12 | 98 | Invention |
| 23 | Example Compound II-3 ($2 \times 10^{-6}$) | 0.12 | 100 | Invention |
| 24 | Example Compound II-4 ($2 \times 10^{-6}$) | 0.13 | 98 | Invention |

In this table, comparative compound *1 is the same as that shown in Table 1.

As is apparent from Table 3, the emulsion of the present invention are low in fogging and have a similarly high sensitivity.

It is very significant in the art that the fogging can be depressed to this extent.

TABLE A

EX-1

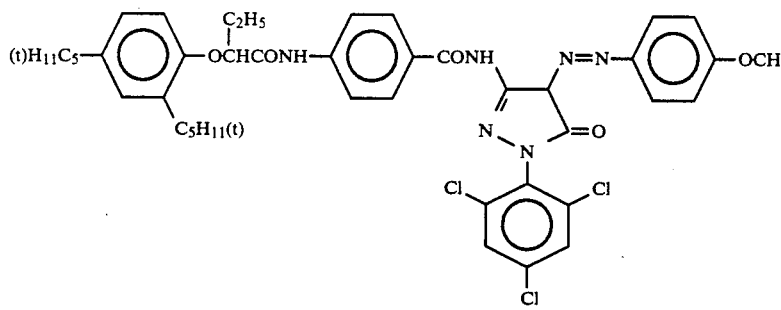

EX-2

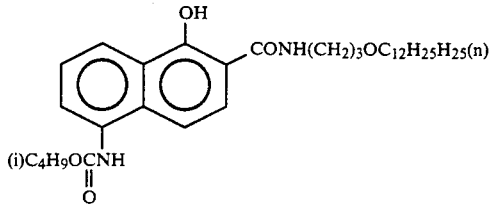

TABLE A -continued
EX-3
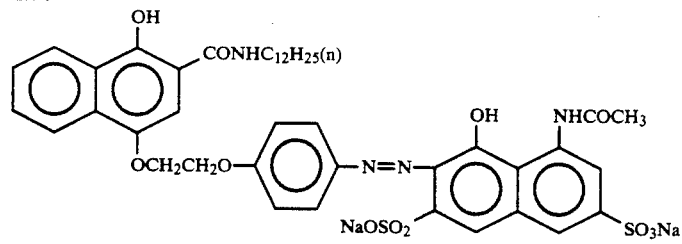
EX-4
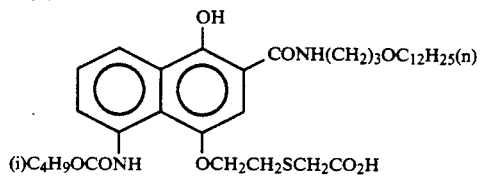
EX-5
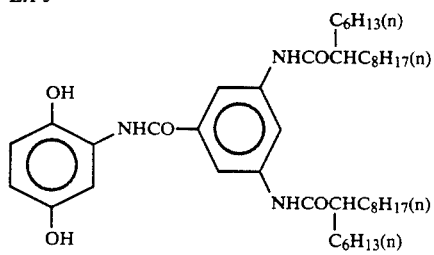
EX-6
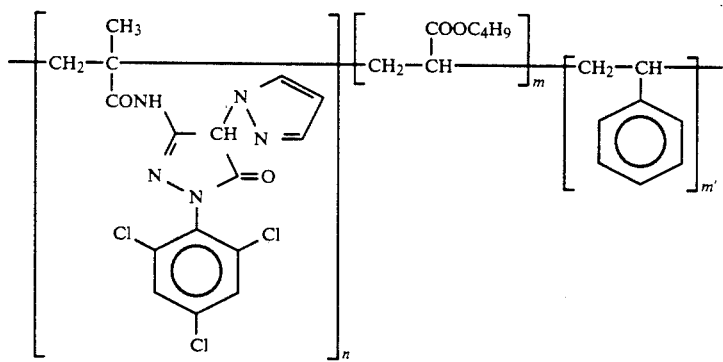
n = 50
m = 25
m' = 25
mol. wt. ca. 20,000
EX-7
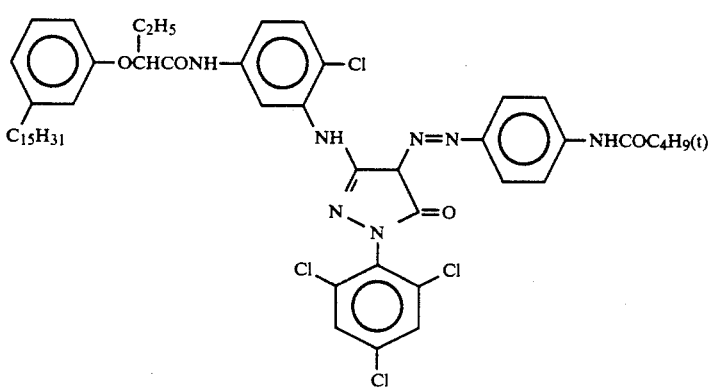

-continued
TABLE A
EX-8
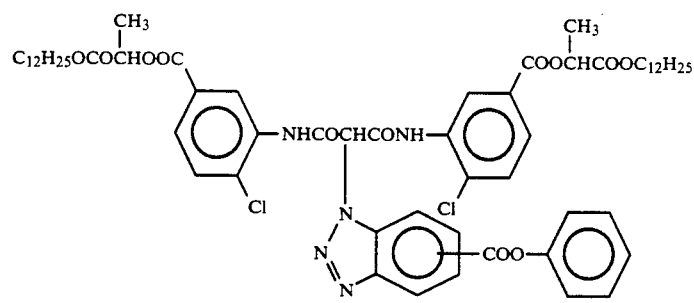
EX-9
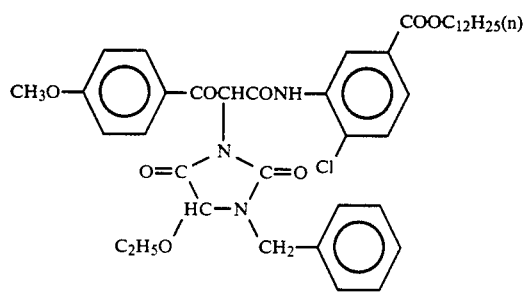
EX-10
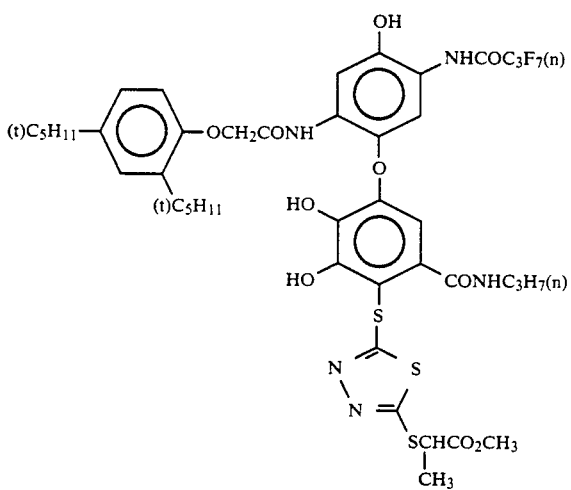
EX-11
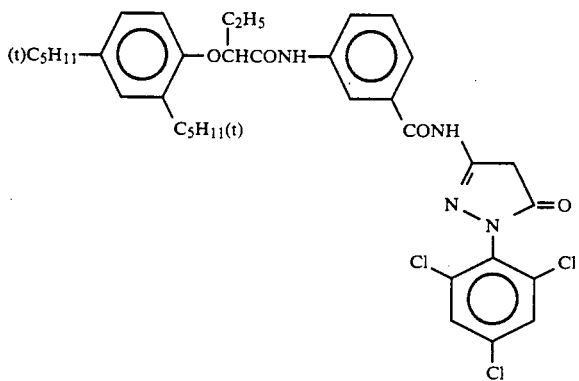
EX-12

TABLE A -continued
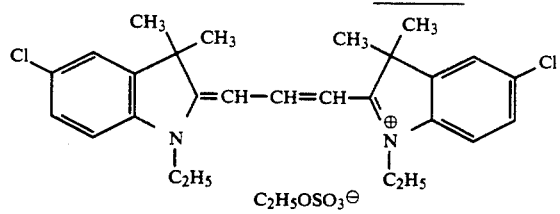
EX-13
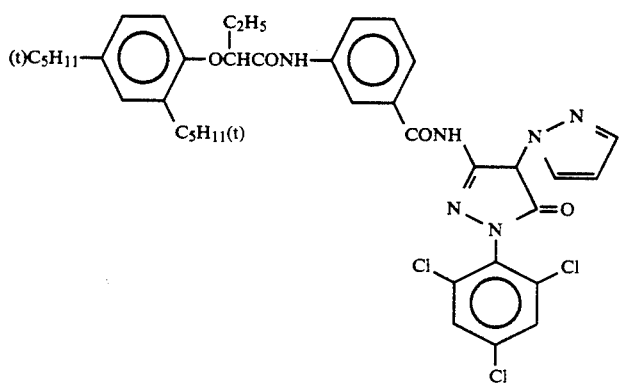
U-1
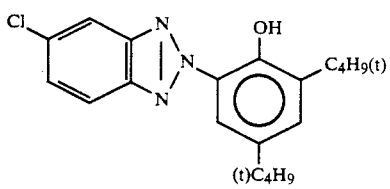
U-2
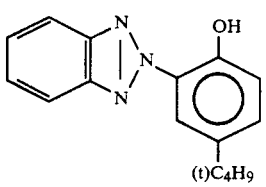
U-3
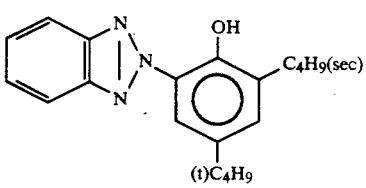
U-4
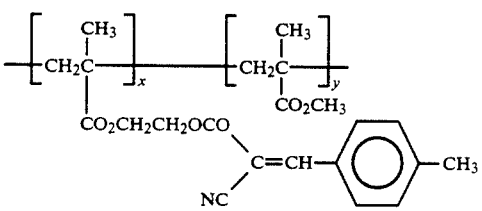
x:y = 70:30 (wt %)
UV-5

TABLE A -continued
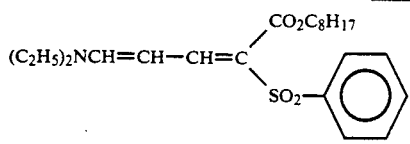
HBS-1  Triscresyl Phosphate
HBS-2  Di-n-butyl Phthalate
HBS-3
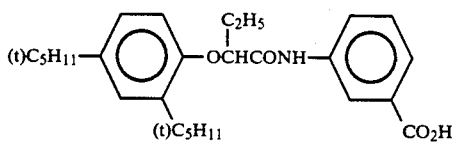
Sensitizing Dye I
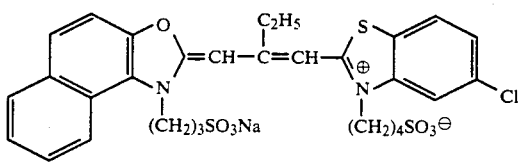
Sensitizing Dye II
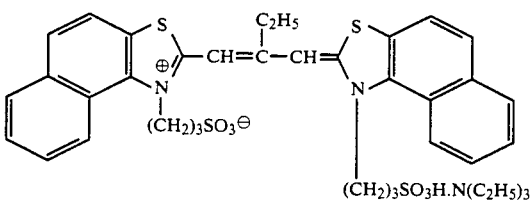
Sensitizing Dye III
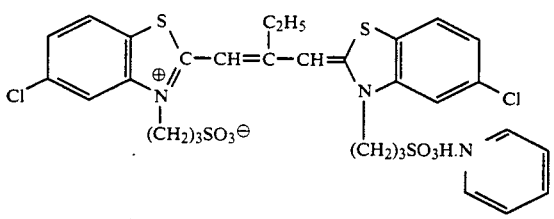
Sensitizing Dye IV
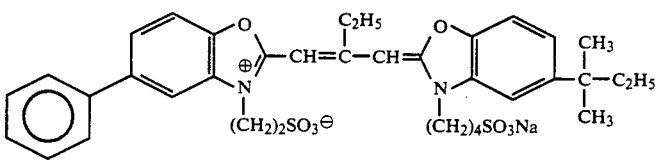
Sensitizing Dye V
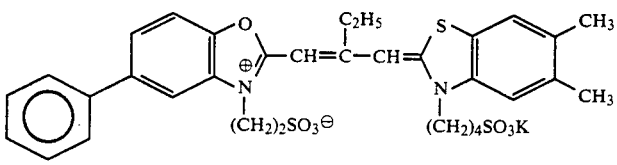
Sensitizing Dye VI TABLE A -continued
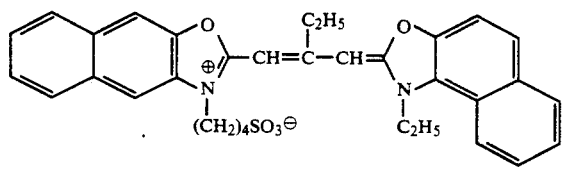
Sensitizing Dye VII
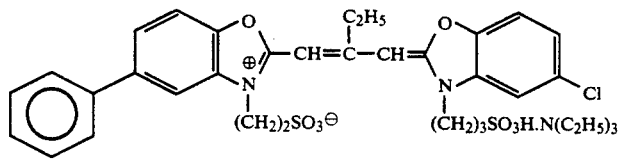
Sensitizing Dye VIII
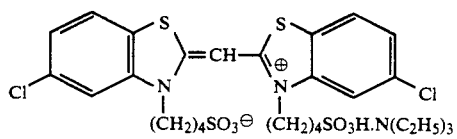
S-1
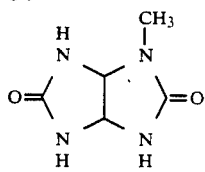
H-1
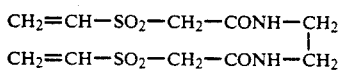
Ex-14
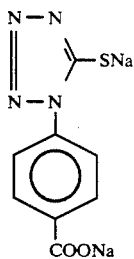
Ex-15
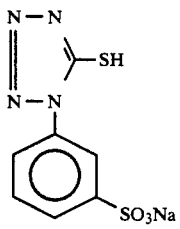
EX-16 Copolymer of Polyvinylpyrrolidone and Polyvinyl Alcohol
Ex-17
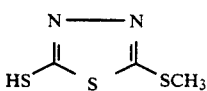
Ex-18

TABLE A -continued

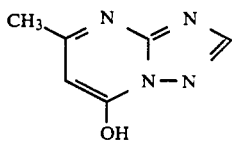

EX-19   1,2-Benzisothiazoline-3-one

EX-20   n-Butyl-p-hydroxybenzoate

EX-21   2-Phenoxyethanol

Ex-22

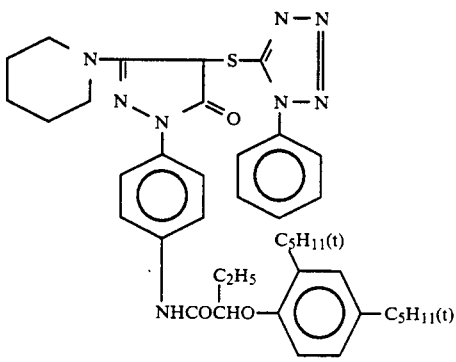

V-1

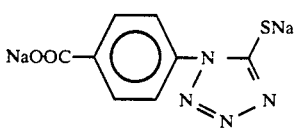

EXAMPLE 4

Preparation of Em-A

One thousand ml of an aqueous solution containing 10.5 g of gelatin and 3.0 g of KBr was kept at 60° C. and stirred. An aqueous solution of silver nitrate ($AgNO_3$: 8.2 g) and an aqueous solution of halides (KBr: 5.7 g and KI: 0.35 g) were added thereto for 1 minute by a double jet method. After 21.5 g of gelatin was added thereto, the temperature was elevated to 75° C. An aqueous solution of silver nitrate ($AgNO_3$: 136.3 g) and an aqueous solution of halides (containing KI in an amount of 4.2 mol % based on KBr) were added accelerating the flow rate by a double jet method for 51 minutes. At this time, the silver potential was maintained at 0 mV to a saturated calomel electrode. The temperature was lowered to 40° C., and an aqueous solution of silver nitrate ($AgNO_3$: 28.6 g) and an aqueous solution of KBr were added thereto for 5.35 minutes by a double jet method. At this time, the silver potential was maintained at $-50$ mV to the saturated calomel electrode. The resulting emulsion was desalted according to the flocculation method, and gelatin was added thereto, followed by adjustment to to pH 5.5 and pAg 8.8. Em-A was an emulsion containing tabular grains having a mean circle-corresponding diameter of 1.14 μm, a mean thickness of 0.189 μm, a mean aspect ratio of 6.03 and a coefficient of variation in circle-corresponding diameter of 28%.

Preparation of Em-B

An emulsion was prepared in the same manner as Em-A with the exception that an aqueous solution of halides containing KI in an amount of 4.2 mol % based on KBr in the second stage was substituted for the aqueous solution of halides containing KI in an amount of 8.4 mol % based on KBr. Em-B was an emulsion containing tabular grains having a mean circle-corresponding diameter of 1.17 μm, a mean thickness of 0.190 μm, a mean aspect ratio of 6.16 and a coefficient of variation in circle-corresponding diameter of 31%.

Preparation of Em-C

The process was conducted in the same manner as the preparation of Em-A until the aqueous solution of silver nitrate in the second stage was added and the temperature was lowered to 40° C. An aqueous solution of silver nitrate ($AgNO_3$: 3.2 g) and an aqueous solution of KI (KI: 2.3 g) were added for 5 minutes. Then, an aqueous solution of silver nitrate ($AgNO_3$: 25.4 g) and an aqueous solution of KBr were added thereto for 5.35 minutes by a double jet method. At this time, the silver potential was maintained at $-50$ mV to the saturated calomel electrode. After the flocculation, the process was conducted in the same manner as the preparation of Em-A. Em-C was an emulsion containing tabular grains having a mean circle-corresponding diameter of 1.09 μm, a mean thickness of 0.196 μm, a mean aspect ratio of 5.56 and a coefficient of variation in circle-corresponding diameter of 29%.

Preparation of Em-D

The process was conducted in the same manner as the preparation of Em-A until the aqueous solution of silver nitrate in the first stage was added and the temperature was elevated to 75° C. Then, an aqueous solution of silver nitrate (AgNO₃: 136.3 g) and an aqueous solution of halides (containing KI in an amount of 4.2 mol % based on KBr) were added accelerating the flow rate by a double jet method for 51 minutes. At this time, the silver potential was maintained at 0 mV to a saturated calomel electrode for the first 46 minutes, and then changed to +90 mV. The temperature was increased to 40° C., and an aqueous solution of silver nitrate (AgNO₃: 3.2 g) and an aqueous solution of KI (KI: 2.3 g) were added thereto for 5 minutes. Then, an aqueous solution of silver nitrate (AgNO₃: 25.4 g) and an aqueous solution of KBr were added thereto for 5.35 minutes by a double jet method. At this time, the silver potential was maintained at −50 mV to the saturated calomel electrode. After the flocculation, the process was conducted in the same manner as the preparation of Em- A. Em-D was an emulsion containing tabular grains having a mean circle-corresponding diameter of 1.21 μm, a mean thickness of 0.197 μm, a mean aspect ratio of 6.14 and a coefficient of variation in circle-corresponding diameter of 27%.

Em-A to Em-D were observed with a 200-kV transmission electron microscope at the liquid nitrogen temperature. As a result, for Em-A and Em-B, no transition line was observed in almost all of the grains. On the other hand, for Em-C, many transition lines were observed throughout the outer peripheral regions of the tabular grains. For Em-D, many transition lines locally dense in the vicinity of the 6 vertices of the hexagonal tabular grains were observed. For both Em-C and Em-D, the mean number of transition lines per grain could not be accurately counted, but 20 or more lines were apparently confirmed.

The above-described emulsions Em-A to Em-D were subjected to chemical ripening in the following manner.

Each of emulsions Em-A to Em-D was divided into 4 parts. After the following sensitizing dye Dye-1 was added in an amount of 1×10⁻³ mol/mol of Ag, sodium thiosulfate, the selenium sensitizer shown in Table 4, compound F-3 (sodium salt of 3-sulfophenylmercaptotetrazole), chloroauric acid and potassium thiocyanate were added in amounts shown in Table 4, respectively, followed by optimal chemical ripening.

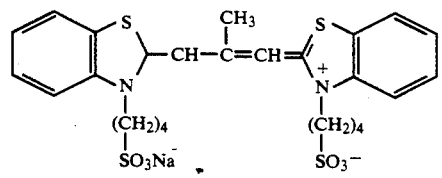

Dye 1

After completion of the chemical ripening, the following compounds were added thereto, and applied together with a protective layer to a support of a triacetyl cellulose film provided with an underlayer by the simultaneous extrusion method.

(1) Emulsion Layer

Emulsion: each emulsion shown in Table 4

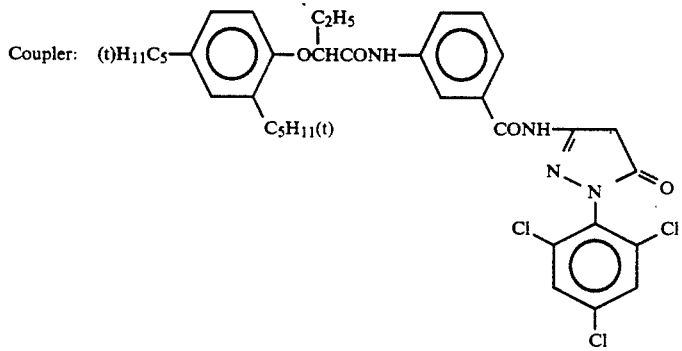

Coupler:

Tricresyl Phosphate
Stabilizer: 4-Hydroxy-6-methyl-1,3,3a,7-tetraazaindene
Coating Assistant: Sodium Dodecylbenzenesulfonate (2) Protective Layer Polymethyl Methacrylate Grains
Sodium Salt of 2,4-Dichloro-6-hydroxy-s-triazine
Gelatin These samples were subjected to exposure for sensitometry for 1/100 second, and then to the following color processing.

The processing was conducted at 38° C. under the following conditions:

| 1. Color Development: | 2 min and 45 sec |
| 2. Bleaching: | 6 min and 30 sec |
| 3. Washing: | 3 min and 15 sec |
| 4. Fixing: | 6 min and 30 sec |
| 5. Washing: | 3 min and 15 sec |
| 6. Stabilizing: | 3 min and 15 sec |

The composition of processing solutions used in respective stages was as follows:

| Color Developing Solution | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N-Ethyl-N-β-hydroxyethylamino)-2-methylaniline Sulfate | 4.5 g |
| Water to make | 1 l |
| Bleaching Solution | |
| Ammonium Bromide | 160.0 g |
| Aqueous Ammonia (28%) | 25.0 ml |

-continued

| | | |
|---|---|---|
| Sodium Ethylenediaminetetraacetate | 130 g | |
| Glacial Acetic Acid | 14 ml | |
| Water to make | 1 l | |
| Fixing Solution | | |
| Sodium Tetrapolyphosphate | 2.0 g | |
| Sodium Sulfite | 15 g | |
| Ammonium Thiosulfate (70%) | 175.0 ml | |
| Sodium Bisulfite | 4.6 g | |
| Water to make | 1 l | |
| Stabilizing Solution | | |
| Formalin | 8.0 ml | |
| Water to make | 1 l | |

Then, the density of the processed samples was measured through a green filter.

Sensitivity is defined as the reciprocal of the exposure giving a density of a fogging value +0.1, and the value of Sample 25 was taken as 100. Table 5 shows fogging values represented by relative values based thereon, and values of sensitivity.

Further, the graininess was evaluated in the following manner. Samples 25 to 40 were subjected to an exposure which gives a density of a fogging value +0.5, and then processed with the above-described processing solutions. Using a microdensitometer, the density of the samples was measured through a green filter to determine the RMS granularity. Taking the RMS granularity of Sample 25 as 100, the results represented by relative values based thereon are shown in Table 5.

In addition, the shelf life was evaluated for these samples. The shelf life was evaluated by storing the samples at a temperature of 50° C. and a relative humidity of 30% for 6 days before the exposure. Increments of fogging values after storage on the basis of those before storage and the sensitivity after storage were represented by relative values taking the values of Sample 25 without storage as 100, and are shown in Table 5.

TABLE 4

Descriptions of Samples of Example 4

| Sample No. | Name of Emulsion | Amount of Sodium Thiosulfate (mol/mol Ag) | Amount of Selenium Sensitizer (mol/mol Ag) |
|---|---|---|---|
| 25 | A (No transition) | $1.1 \times 10^{-5}$ | — |
| 26 | A (No transition) | $1.0 \times 10^{-5}$ | N,N,N'.N'-Tetramethyl-selenourea $1.0 \times 10^{-5}$ |
| 27 | A (No transition) | $1.0 \times 10^{-5}$ | Example Compound I-2 $0.8 \times 10^{-5}$ |
| 28 | A (No transition) | $1.0 \times 10^{-5}$ | Example Compound III-3 $0.7 \times 10^{-5}$ |
| 29 | B (No transition) | $1.1 \times 10^{-5}$ | — |
| 30 | B (No transition) | $1.0 \times 10^{-5}$ | N,N,N'.N'-Tetramethyl-selenourea $1.0 \times 10^{-5}$ |
| 31 | B (No transition) | $1.0 \times 10^{-5}$ | Example Compound I-2 $0.8 \times 10^{-5}$ |
| 32 | B (No transition) | $1.0 \times 10^{-5}$ | Example Compound III-3 $10.7 \times 10^{-5}$ |
| 33 | C (No transition) | $1.1 \times 10^{-5}$ | — |
| 34 | C (No transition) | $1.0 \times 10^{-5}$ | N,N,N'.N'-Tetramethyl-selenourea $1.0 \times 10^{-5}$ |
| 35 | C (No transition) | $1.0 \times 10^{-5}$ | Example Compound I-2 $0.8 \times 10^{-5}$ |
| 36 | C (No transition) | $1.0 \times 10^{-5}$ | Example Compound III-3 $0.7 \times 10^{-5}$ |
| 37 | D (No transition) | $1.1 \times 10^{-5}$ | — |
| 38 | D (No transition) | $1.0 \times 10^{-5}$ | N,N,N'.N'-Tetramethyl-selenourea $1.0 \times 10^{-5}$ |
| 39 | D (No transition) | $1.0 \times 10^{-5}$ | Example Compound I-2 $0.8 \times 10^{-5}$ |
| 40 | D (No transition) | $1.0 \times 10^{-5}$ | Example Compound III-3 $0.7 \times 10^{-5}$ |

| Sample No. | Amount of Antifoggant F-3 (mol/mol Ag) | Amount of Chloroauric Acid (mol/mol Ag) | Amount of Potassium Thiocyanate (mol/mol Ag) |
|---|---|---|---|
| 25 | $7 \times 10^{-5}$ | $1.0 \times 10^{-5}$ | $8.0 \times 10^{-4}$ |
| 26 | $1 \times 10^{-4}$ | $1.5 \times 10^{-5}$ | $2.4 \times 10^{-3}$ |
| 27 | $1 \times 10^{-4}$ | $1.5 \times 10^{-5}$ | $2.4 \times 10^{-3}$ |
| 28 | $1 \times 10^{-4}$ | $1.5 \times 10^{-5}$ | $2.4 \times 10^{-3}$ |
| 29 | $7 \times 10^{-5}$ | $1.0 \times 10^{-5}$ | $8.0 \times 10^{-4}$ |
| 30 | $1 \times 10^{-4}$ | $1.5 \times 10^{-5}$ | $2.4 \times 10^{-3}$ |
| 31 | $1 \times 10^{-4}$ | $1.5 \times 10^{-5}$ | $2.4 \times 10^{-3}$ |
| 32 | $1 \times 10^{-4}$ | $1.5 \times 10^{-5}$ | $2.4 \times 10^{-3}$ |
| 33 | $7 \times 10^{-5}$ | $1.0 \times 10^{-5}$ | $8.0 \times 10^{-4}$ |
| 34 | $1 \times 10^{-4}$ | $1.5 \times 10^{-5}$ | $2.4 \times 10^{-3}$ |
| 35 | $1 \times 10^{-4}$ | $1.5 \times 10^{-5}$ | $2.4 \times 10^{-3}$ |
| 36 | $1 \times 10^{-4}$ | $1.5 \times 10^{-5}$ | $2.4 \times 10^{-3}$ |
| 37 | $7 \times 10^{-5}$ | $1.0 \times 10^{-5}$ | $8.0 \times 10^{-4}$ |
| 38 | $1 \times 10^{-4}$ | $1.5 \times 10^{-5}$ | $2.4 \times 10^{-3}$ |
| 39 | $1 \times 10^{-4}$ | $1.5 \times 10^{-5}$ | $2.4 \times 10^{-3}$ |
| 40 | $1 \times 10^{-4}$ | $1.5 \times 10^{-5}$ | $2.4 \times 10^{-3}$ |

TABLE 5

Results of Example 4

| Sample No. | Fogging | Sensitivity | Graininess | Increase in Fogging after Storage | Sensitivity after Storage | Relation to This Application |
|---|---|---|---|---|---|---|
| 25 | 0.20 | 100 | 100 | 0.05 | 79 | Comparison |
| 26 | 0.49 | 112 | 110 | 0.16 | 80 | Comparison |
| 27 | 0.23 | 126 | 110 | 0.11 | 99 | Comparison |
| 28 | 0.23 | 126 | 109 | 0.12 | 99 | Comparison |
| 29 | 0.23 | 107 | 95 | 0.05 | 85 | Comparison |
| 30 | 0.50 | 120 | 99 | 0.15 | 90 | Comparison |
| 31 | 0.25 | 135 | 100 | 0.10 | 110 | Comparison |
| 32 | 0.26 | 138 | 100 | 0.09 | 114 | Comparison |
| 33 | 0.19 | 123 | 95 | 0.04 | 106 | Comparison |
| 34 | 0.25 | 154 | 96 | 0.06 | 138 | Comparison |
| 35 | 0.13 | 158 | 96 | 0.02 | 150 | Invention |
| 36 | 0.13 | 158 | 95 | 0.02 | 149 | Invention |
| 37 | 0.19 | 129 | 95 | 0.03 | 106 | Comparison |
| 38 | 0.26 | 162 | 96 | 0.06 | 136 | Comparison |
| 39 | 0.14 | 166 | 96 | 0.02 | 162 | Invention |
| 40 | 0.14 | 162 | 95 | 0.02 | 158 | Invention |

As is apparent from Table 5, the emulsions which have been selenium sensitized with the compounds used in the present invention can achieve an increase in sensitivity without an increase in fogging. Further, compared to the grains having no transition lines, the grains having transition lines can achieve low fogging and very high sensitivity.

The results reveals that the emulsions according to the present invention have good graininess as well as high sensitivity, and are also significantly excellent in shelf life.

According to the present invention, compared to the selenium sensitization using the conventional selenium compounds, the generation of the fogging can be depressed and a similarly high degree of sensitivity can be achieved.

While the invention has been described in detail and with reference to specific embodiments thereof, it will be apparent to one skilled in the art that various changes and modifications can be made therein without departing from the spirit and scope thereof.

What is claimed is:

1. A silver halide photographic material low in fogging generation and high in sensitivity comprising a silver halide emulsion selenium sensitized with at least one compound selected from the group consisting of compounds represented by general formula (I) or (III):

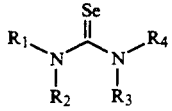
(I)

wherein each of $R_1$, $R_2$, $R_3$ and $R_4$ represents an alkyl group, a cycloalkyl group, an alkenyl group, an alkynyl group, an aralkyl group, an aryl group, a heterocyclic group, an acyl group, an alkoxycarbonyl group, an aryloxycarbonyl group, a carbamoyl group or a sulfamoyl group, provided that a tetramethylselenourea is excluded;

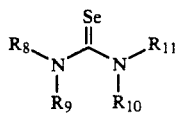
(III)

wherein each of $R_8$, $R_9$, $R_{10}$ and $R_{11}$ represents a hydrogen atom, an alkyl group, a cycloalkyl group, an alkenyl group, an alkynyl group, an aralkyl group, an aryl group, a heterocyclic group, an acyl group, a carboxyl group, a formyl group, an alkoxycarbonyl group, an aryloxycarbonyl group, or a sulfamoyl group, provided that at least one pair of $R_8$ and $R_9$, $R_9$ and $R_{10}$, $R_{10}$ and $R_{11}$, and $R_{11}$ and $R_8$ combine to form a ring; wherein the alkyl group is unsubstituted or is substituted with an alkyl, cycloalkyl, heterocyclic, acyl, alkoxycarbonyl, aryloxycarbonyl, acyloxy, amino, ammonio, acylamino, carbamoyl, sulfonylamino, sulfamoyl, alkoxy, aryloxy, alkylthio, arylthio, sulfonyl, sulfinyl, sulfo, sulfino, hdyroxyl, halogen, cyano, nitro, ureido, phosphono or mercapto group.

2. A silver halide photographic material comprising a silver halide emulsion selenium sensitized with at least one compound selected from the group consisting of compounds represented by the following general formula (I):

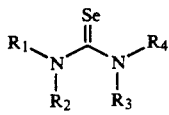
(I)

wherein each of $R_1$, $R_2$, $R_3$ and $R_4$ represents an alkyl group, a cycloalkyl group, an alkenyl group, an alkynyl group, an aralkyl group, an aryl group, a heterocyclic group, an acyl group, an alkoxycarbonyl group, an aryloxycarbonyl group, a carbamoyl group or a sulfamoyl group, provided that is a tetramethylselenourea is excluded; wherein the alkyl group is unsubstituted or is substituted with an alkyl, cycloalkyl, heterocyclic, acyl, alkoxycarbonyl, aryloxycarbonyl, acyloxy, amino, ammonio, acylamino, carbamoyl, sulfonylamino, sulfamoyl, alkoxy, aryloxy, alkylthio, arylthio, sulfonyl, sulfinyl, sulfo, sulfino, hdyroxyl, halogen, cyano, nitro, ureido, phosphono or mercapto group.

3. A silver halide photographic material comprising a silver halide emulsion selenium sensitized with at least one compound selected from the group consisting of compounds represented by the following general formula (III):

(III)

wherein each of $R_8$, $R_9$, $R_{10}$ and $R_{11}$ represents a hydrogen atom, an alkyl group, a cycloalkyl group, an alkenyl group, an alkynyl group, an aralkyl group, an aryl group, a heterocyclic group, an acyl group, a formyl group, an alkoxycarbonyl group, an aryloxycarbonyl group, a carbamoyl group or a sulfamoyl group, provided that at least one pair of $R_8$ and $R_9$, $R_9$ and $R_{10}$, $R_{10}$ and $R_{11}$, and $R_{11}$ and $R_8$ combine to form a ring; wherein the alkyl group is unsubstituted or is substituted with an alkyl, cycloalkyl, heterocyclic, acyl, alkoxycarbonyl, aryloxycarbonyl, acyloxy, amino, ammonio, acylamino, carbamoyl, sulfonylamino, sulfamoyl, alkoxy, aryloxy, alkylthio, arylthio, sulfonyl, sulfinyl, sulfo, sulfino, hdyroxyl, halogen, cyano, nitro, ureido, phosphono or mercapto group.

4. A silver halide photographic material as claimed in claim 2, wherein said emulsion comprises grains of silver chloroiodobromide, silver iodobromide, silver chlorobromide or silver bromide, said grain having an aspect ratio of at least 3 and having at least one transition line therein.

5. A silver halide photographic material as claimed in claim 4, wherein said general formula (I) is represented by the following general formula (II):

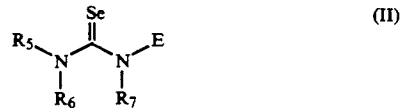
(II)

wherein each of $R_5$, $R_6$, $R_7$ and E represents an alkyl group, a cycloalkyl group, an alkenyl group, an alkynyl group, an aralkyl group, an aryl group, a heterocyclic group, an acyl group, an alkoxycarbonyl group, an aryloxycarbonyl group, a carbamoyl group or a sulfamoyl group, provided E has a p value of Hammett's constituent constant of $-0.1$ or more.

6. A silver halide photographic material as claimed in claim 3, wherein said emulsion comprises grains of silver chloroiodobromide, silver iodobromide, silver chlorobromide or silver bromide, said grain having an aspect ratio of at least 3 and having at least one transition line therein.

7. A silver halide photographic material as claimed in claim 5, wherein each of $R_1$, $R_2$, and $R_3$ represents a substituted or unsubstituted alkyl group, a substituted or unsubstituted aryl group, a substituted or unsubstituted acyl group, and E represents an acyl group having op of Hammet's substituent constant of 0.3 or more.

8. A silver halide photographic material as claimed in claim 3, wherein the ring formed by a pair of R groups is a 5-membered or 6-membered ring, and each of $R_8$, $R_9$, $R_{10}$ and $R_{11}$ is a hydrogen atom, a substituted or unsubstituted alkyl group, a substituted or unsubstituted aryl group.

9. A silver halide photographic material as claimed in claim 1, wherein the emulsion has also been subjected to noble metal sensitization.

10. A silver halide photographic material as claimed in claim 9, wherein the noble metal sensitization is gold sensitization.

* * * * *